United States Patent [19]

Kukla et al.

[11] Patent Number: 5,270,464

[45] Date of Patent: Dec. 14, 1993

[54] ANTI-HIV-1 TETRAHYDROIMIDAZO[1,4]BENZODIAZEPIN-2-(THI)ONES

[75] Inventors: Michael J. Kukla, Maple Glen; Henry J. Breslin, Lansdale, both of Pa.; Alfons H. M. Raeymaekers, Beerse, Belgium; Josephus L. H. Van Gelder, Kasterlee, Belgium; Paul A. J. Janssen, Vosselaar, Belgium

[73] Assignee: Janssen Pharmaceutica N.V., Beerse, Belgium

[21] Appl. No.: 42,858

[22] Filed: Apr. 5, 1993

Related U.S. Application Data

[63] Continuation of Ser. No. 671,238, Mar. 19, 1991, abandoned, which is a continuation-in-part of Ser. No. 583,533, Sep. 17, 1990, abandoned, which is a continuation-in-part of Ser. No. 323,585, Mar. 14, 1989, abandoned, and a continuation-in-part of Ser. No. 476,926, Feb. 8, 1990, abandoned, which is a continuation-in-part of Ser. No. 406,626, Sep. 13, 1989, abandoned, and a continuation-in-part of Ser. No. 549,349, Jul. 6, 1990, abandoned, and a continuation-in-part of Ser. No. 549,777, Jul. 9, 1990, abandoned, which is a continuation-in-part of Ser. No. 406,625, Sep. 13, 1989, abandoned.

[51] Int. Cl.$^5$ .................. C07D 487/08; A61K 31/55
[52] U.S. Cl. ........................................ 540/556
[58] Field of Search ..................... 540/556; 514/220

[56] References Cited

FOREIGN PATENT DOCUMENTS 336466  10/1989  European Pat. Off. .

OTHER PUBLICATIONS

Kukla et al., J. Med. Chem., 34, (1991), pp. 746-751.
P. Geneste et al., Eur. J. Med. Chem.-Chimica Therapeutica, Jan.-Feb., 1978-13, No. 1, pp. 53-59.
Pauwels et al., Nature, vol. 343, Feb. 1, 1990, pp. 470-474.
Koyanagi et al., Int. J. Cancer: 36, 445-451 (1985).

Primary Examiner—Mukund J. Shah
Assistant Examiner—Philip I. Datlow
Attorney, Agent, or Firm—Charles J. Metz

[57] ABSTRACT

Novel tetrahydroimidazo[1,4]benzodiazepin-2-(thi)ones possessing anti-HIV-1 activity, compositions containing these compounds as active ingredients, and methods of treating subjects suffering from HIV-1 infection by administering these compounds. The compounds have the basic structure shown in Formula (I):

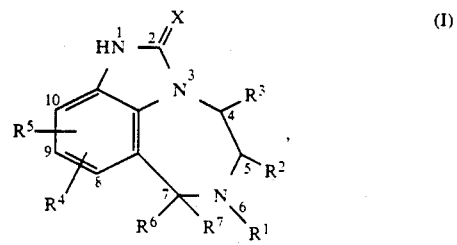

11 Claims, No Drawings

ANTI-HIV-1 TETRAHYDROIMIDAZO[1,4]BENZODIAZEPIN-2-(THI) ONES

CROSS-REFERENCE TO RELATED APPLICATION

This is a continuation of application Ser. No. 671,238, filed Mar. 19, 1991, now abandoned. Ser. No. 671,238 is a continuation-in-part of our co-pending application Ser. No. 583,533 filed Sep. 17, 1990, now abandoned, which in turn is a continuation-in-part of Ser. No. 323,585, filed Mar. 14, 1989, now abandoned; and of Ser. No. 476,926, filed Feb. 8, 1990, now abandoned which is a continuation-in-part of Ser. No. 406,626 filed Sep. 13, 1989, now abandoned; and of Ser. No. 549,349, filed Jul. 6, 1990, now abandoned; and of Ser. No. 549,777, filed Jul. 9, 1990, now abandoned, which is a continuation-in-part of Ser. No. 406,625 filed Sep. 13, 1989, now abandoned.

BACKGROUND OF THE INVENTION

In the Eur. J. Med. Chem. 1978, 13, 53–59, there are described three tetrahydroimidazo[4,5,1-jk][1,4]benzodiazepines. The compounds of the present invention differ therefrom by the fact that the imidazo-moiety is substituted with an oxo or thio group and that said compounds show antiviral activity.

DESCRIPTION OF THE INVENTION

The present invention is concerned with tetrahydroimidazo[1,4]benzodiazepin-2-(thi)ones having the formula:

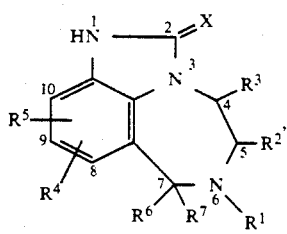

(I)

the pharmaceutically acceptable acid addition salts and the stereochemically isomeric forms thereof, wherein:

X is O or S;
$R^1$ is $C_{1-6}$alkyl optionally substituted with aryl; $C_{3-6}$alkynyl; $C_{3-6}$cycloalkyl; or a radical of formula:

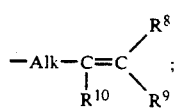

(a-1)

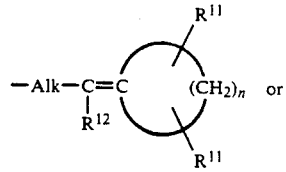

(a-2)

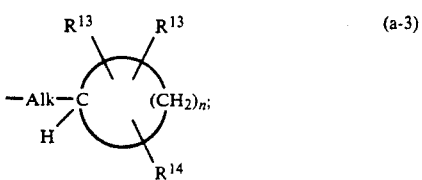

(a-3)

Alk is $C_{1-6}$alkanediyl;
$R^8$ and $R^9$ each independently are hydrogen, halo, $C_{3-6}$cycloalkyl, trifluoromethyl, 2,2,2-trifluoroethyl, $C_{1-4}$alkyl optionally substituted with $C_{1-4}$alkyloxy;
$R^{10}$ is hydrogen, halo or $C_{1-4}$alkyl; each $R^{11}$ independently is hydrogen or $C_{1-4}$alkyl; or both $R^{11}$ taken together may form a $C_{1-6}$alkanediyl radical;
$R^{12}$ is hydrogen, halo or $C_{1-4}$alkyl; n is 2, 3, 4, 5 or 6; each $R^{13}$ independently is hydrogen or $C_{1-4}$alkyl; or both $R^{13}$ taken together may form a $C_{1-6}$alkanediyl radical;
$R^{14}$ is hydrogen or $C_{2-6}$alkenyl;
$R^2$ is hydrogen or methyl;
$R^3$ is hydrogen or $C_{1-6}$alkyl;
$R^4$ and $R^5$ each independently are hydrogen, $C_{1-6}$alkyl, halo, cyano, nitro, trifluoromethyl, hydroxy, $C_{1-6}$alkyloxy, amino, mono-or di($C_{1-6}$alkyl)amino or $C_{1-6}$alkylcarbonylamino;
$R^6$ is hydrogen or methyl;
$R^7$ is hydrogen or methyl;
each aryl is phenyl optionally substituted with from 1 to 3 substituents independently selected from $C_{1-6}$alkyl, halo, hydroxy, $C_{1-6}$alkyloxy, amino, nitro and trifluoromethyl.

The compounds of formula (I) may also exist in their tautomeric form. Said tautomeric form, indicated below, is intended to be included within the scope of the present invention.

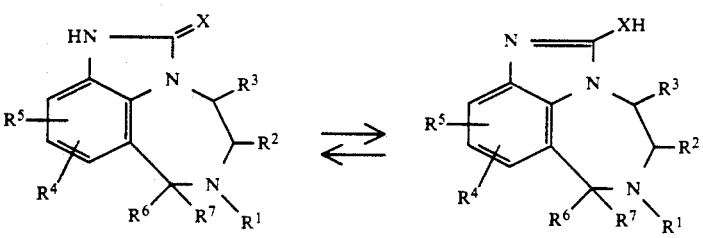

In the foregoing definitions the term halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl, 1,1-dimethylethyl and the like; $C_{1-6}$alkyl defines $C_{1-4}$alkyl radicals as defined hereinabove and the higher homologs thereof having from 5 to 6 carbon atoms; $C_{1-6}$alkanediyl defines bivalent straight or branched chain hydrocarbon radicals containing 1 to 6 carbon atoms such as, for example, 1,2-ethanediyl, 1,3-propanediyl, 1,4-butanediyl, 1,5-pentanediyl, 1,6-hexanediyl and the branched isomers thereof; $C_{2-6}$alkenyl defines straight and branched hydrocarbon radicals containing one double bond and having from 2 to 6 carbon atoms such as, for example, ethenyl, 2-propenyl, 2-butenyl, 3-butenyl, 2-methyl-2-propenyl, pentenyl, hexenyl and the like; $C_{3-6}$alkynyl defines straight and branched chain hydrocarbon radicals containing a triple bond and having from 3 to 6 carbon atoms such as, for example, 2-propynyl, 2-butynyl, 3-butynyl, pentynyl, hexynyl and the like; $C_{3-6}$cycloalkyl defines cyclopropyl, cyclobutyl, cyclopentyl and cyclohexyl.

Each $R^{11}$, $R^{13}$ and $R^{14}$ in the radicals of formula (a-2) and (a-3), when being as defined hereinbefore but other than hydrogen, is meant to replace a hydrogen atom of the $-(CH_2)_n-$ or the $-CH-$ moiety in said radicals.

Depending on the nature of the various substituents, the compounds of formula (I) may have several asymmetric carbon atoms. Unless otherwise mentioned or indicated, the chemical designation of compounds denotes the mixture of all possible stereochemically isomeric forms, said mixtures containing all diastereomers and enantiomers of the basic molecular structure. The absolute configuration of each chiral center may be indicated by the stereochemical descriptors R and S, this R and S notation corresponding to the rules described in Pure Appl. Chem. 1976, 45, 11–30. Stereochemically isomeric forms of the compounds of formula (I) are obviously intended to be embraced within the scope of the invention.

The compounds of formula (I) have basic properties and, consequently, they may be converted to their therapeutically active non-toxic acid addition salt forms by treatment with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term pharmaceutically acceptable acid addition salts also comprises the solvates which the compounds of formula (I) may form and said solvates are intended to be included within the scope of the present invention. Examples of such solvates are e.g. the hydrates, alcoholates and the like.

A first interesting group of compounds of formula (I) are those wherein $R^1$ is $C_{1-6}$alkyl, $C_{3-6}$alkenyl, $C_{3-6}$alkynyl, $C_{3-6}$cycloalkyl or $C_{1-6}$alkyl substituted with $C_{3-6}$cycloalkyl; and/or $R^4$ and $R^5$ each independently are hydrogen, $C_{1-6}$alkyl, halo, cyano, nitro, trifluoromethyl, hydroxy, $C_{1-6}$alkyloxy, amino or mono- or di($C_{1-6}$alkyl)amino; and/or $R^6$ and $R^7$ are hydrogen; and $R^2$, $R^3$, X and aryl are as defined under formula (I).

A second interesting group of compounds of formula (I) are those wherein $R^1$ is $C_{1-6}$alkyl, $C_{3-6}$alkenyl, $C_{3-6}$alkynyl, $C_{3-6}$cycloalkyl or $C_{1-6}$alkyl substituted with $C_{3-6}$cycloalkyl; and/or $R^4$ and $R^5$ each independently are hydrogen, $C_{1-6}$alkyl, halo, cyano, nitro, trifluoromethyl, hydroxy, $C_{1-6}$alkyloxy, amino or mono- or di($C_{1-6}$alkyl)amino; and/or $R^6$ is methyl, $R^7$ is hydrogen; and $R^2$, $R^3$, X and aryl are as defined under formula (I).

More interesting compounds are those compounds of formula (I) or those compounds comprised within the abovementioned interesting groups, wherein $R^1$ is $C_{1-6}$alkyl, $C_{3-6}$alkynyl or a radical of formula (a-1), (a-2) or (a-3); and/or $R^4$ and $R^5$ each independently are hydrogen, $C_{1-6}$alkyl, halo, cyano, nitro, amino, trifluoromethyl, hydroxy or $C_{1-6}$alkyloxy.

A first particular subgroup comprises those more interesting compounds wherein $R^2$ and $R^3$ each independently are hydrogen or methyl; and/or X is O.

A second particular subgroup comprises those more interesting compounds wherein $R^2$ and $R^3$ each independently are hydrogen or methyl; and/or X is S.

More particular compounds are those compounds comprised within the abovementioned particular subgroups wherein $R^1$ is $C_{3-6}$alkyl or a radical of formula (a-1) wherein $R^8$ and $R^9$ each independently are $C_{3-6}$cycloalkyl, trifluoromethyl or $C_{1-4}$alkyl; or a radical of formula (a-3) wherein n is 2 or 3; and/or $R^5$ and $R^7$ are hydrogen.

Preferred compounds are those more particular compounds wherein $R^8$ and $R^9$ each independently are $C_{1-3}$alkyl; and/or each $R^{13}$ and $R^{14}$ are hydrogen; and/or $R^6$ is hydrogen.

More preferred compounds are those preferred compounds wherein $R^1$ is propyl; 3,3-dimethylbutyl; methylcyclopropyl optionally substituted with one or two methyl groups and/or one 2-methylpropenyl group; methylcyclobutyl; 2-propenyl; 2-butenyl; 2-methyl-2-butenyl; 3-methyl-2-butenyl, 2,3-dimethyl-2-butenyl or 3-ethyl-2-pentenyl; and/or $R^4$ is hydrogen, methyl, chloro or bromo.

The most preferred compounds are (+)-(S)-9-chloro-4,5,6,7-tetrahydro-5-methyl-6-(3-methyl-2-butenyl)imidazo[4,5,1-jk][1,4]benzodiazepine-2(1H)-thione;

(+)-(S)-4,5,6,7-tetrahydro-5,8-dimethyl-6-(3-methyl-2-butenyl)imidazo[4,5,1-jk][1,4]benzodiazepine-2(1H)-thione;

(+)-(S)-8-bromo-4,5,6,7-tetrahydro-5-methyl-6-(3-methyl-2-butenyl)imidazo[4,5,1-jk][1,4]benzodiazepine-2(1H)-thione;

(+)-(S)-8-chloro-6-(3-ethyl-2-pentenyl)-4,5,6,7-tetrahydro-5-methylimidazo[4,5,1-jk][1,4]benzodiazepine-2(1H)-thione and (+)-(S)-8-chloro-4,5,6,7-tetrahydro-5-methyl-6-(3-methyl-2-butenyl)imidazo[4,5,1-jk][1,4]benzodiazepine-2(1H)-thione.

In the following paragraphs, there are described different ways of preparing compounds of formula (I).

The compounds of formula (I) can generally be prepared by condensing a 9-amino-2,3,4,5-tetrahydro-1H-1,4-benzodiazepine of formula (II) with a reagent of formula (III), wherein L is an appropriate leaving group.

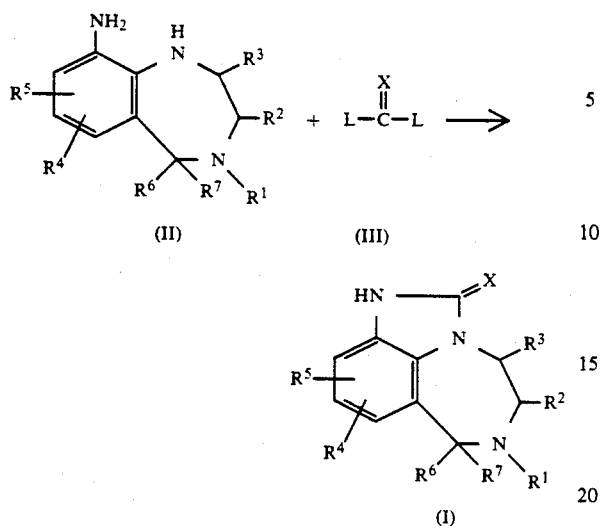

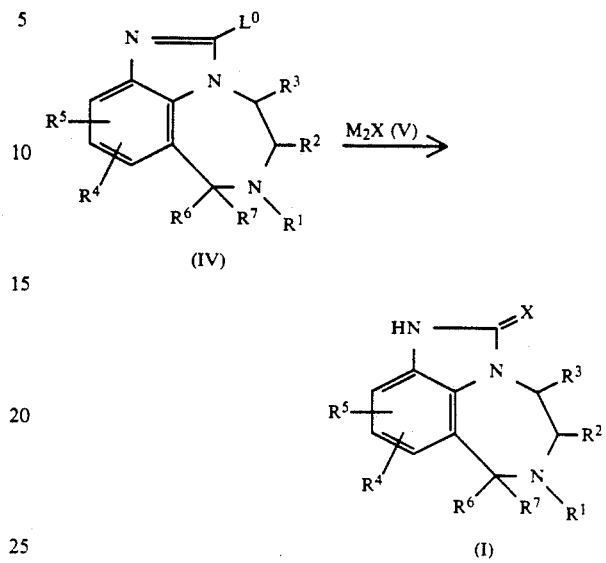

a reagent of formula $M_2X$ (V), wherein X is as defined hereinabove.

In formula (IV), $L^0$ is a reactive leaving group such as, for example, halo, e.g. chloro, bromo and the like groups. Appropriate reagents of formula $M_2X$ (V) are for example, water, urea, thiourea, alkali metal thiosulfates, e.g. sodium thiosulfate and the like reagents. Said reaction can conveniently be conducted by stirring and optionally heating the reactants in a reaction-inert solvent such as, for example, water, an alkanol, e.g., methanol, ethanol, 1-propanol, 2-propanol, butanol, 1,2-ethanediol and the like; or an aromatic hydrocarbon, e.g. benzene, methylbenzene, dimethylbenzene and the like; a halogenated hydrocarbon, e.g. trichloromethane, tetrachloromethane, chlorobenzene and the like; an ether, e.g. tetrahydrofuran, 1,4-dioxane, 1,1'-oxybisbutane, 1,1'-oxybis(2-methoxyethane), 1,2-bis(2-methoxyethoxy)ethane and the like; a dipolar aprotic solvent, e.g. N,N-dimethylformamide, N,N-dimethylacetamide, dimethyl sulfoxide, 1-methyl-2-pyrrolidinone, pyridine, methylpyridine, dimethylpyridine, tetrahydrothiophene 1,1-dioxide and the like; or a mixture of such solvents. In some cases it may be appropriate to conduct said reaction in an excess of the reagent of formula (V), optionally in the presence of a reaction-inert solvent as defined above. In particular, the reaction may be conducted at an elevated temperature, more particularly the reflux temperature of the reaction mixture. Further, it may be appropriate to add to the reaction mixture a base such as, for example, an amine, e.g. N,N-diethylethanamine, N-ethyl-N-(1-methylethyl)-2-propanamine, 4-methylmorpholine and the like amines.

The compounds of formula (I) can also be obtained by N-alkylating an intermediate of formula (VI) with a reagent of formula $R^1$—W (VII) wherein W represents an appropriate reactive leaving group such as, for example, halo, e.g. chloro, bromo or iodo; or a sulfonyloxy group, e.g. benzenesulfonyloxy, 4-methylbenzenesulfonyloxy, methanesulfonyloxy and the like.

Appropriate agents of formula (III) are for example urea, di($C_{1-6}$alkyl)carbonate, carbonoic dichloride, trichloromethyl chloroformate, 1,1'-carbonylbis[1H-imidazole], alkali metal, alkaline earth metal or ammonium isocyanates, phenyl isocyanate, benzoyl isocyanate, thiourea, carbonothioic dichloride, carbon disulfide, 1,1'-carbonothioylbis[1H-imidazole], xanthogenates, alkali metal, alkaline earth metal or ammonium isothiocyanates, phenyl isothiocyanate, benzoyl isothiocyanate, 1,3-dithiolane-2-thione and the like. Said condensation reaction may conveniently be conducted by stirring and optionally heating the reactants in a reaction-inert solvent, such as, for example, an aromatic hydrocarbon, e.g. benzene, methylbenzene, dimethylbenzene and the like; a halogenated hydrocarbon, e.g. trichloromethane, tetrachloromethane, chlorobenzene and the like; an ether, e.g. tetrahydrofuran, 1,4-dioxane, 1,1'-oxybisbutane, 1,1'-oxybis(2-methoxyethane), 1,2-bis(2-methoxyethoxy)ethane and the like; a dipolar aprotic solvent, e.g. N,N-dimethylformamide, N,N-dimethylacetamide, dimethyl sulfoxide, 1-methyl-2-pyrrolidinone, pyridine, methylpyridine, dimethylpyridine, tetrahydrothiophene 1,1-dioxide and the like; or a mixture of such solvents. In some instances however, it may be preferable to heat the reactants without a solvent. Further it may be appropriate to add to the reaction mixture a base such as, for example, a tertiary amine, e.g. N,N-diethylethanamine, N-ethyl-N-(1-methylethyl)-2-propanamine, 4-methylmorpholine and the like amines. When said reagent of formula (III) is carbon disulfide, the reaction can also be conducted conveniently in an alkanol such as, for example, methanol, ethanol, propanol and the like, in the presence of a base such as sodium or potassium hydroxide and the like or in carbon disulfide as solvent and in the presence of a suitable base such as, for example, an alkyl magnesium halide, e.g. ethyl magnesium bromide, an alkyl lithium, e.g. butyllithium, an amine, e.g., N,N-diethylethanamine, a carbodiimide, e.g. N,N-dicyclohexylcarbodiimide and the like reagents. Or, alternatively the latter reaction may also be conducted in basic solvent such as, for example, pyridine and the like, in the presence of a phosphite such as, for example, diphenylphosphite.

The compounds of formula (I) can also be prepared by reacting a 4,5,6,7-tetrahydroimidazo[4,5,1-jk][1,4]benzodiazepine derivative of formula (IV) with

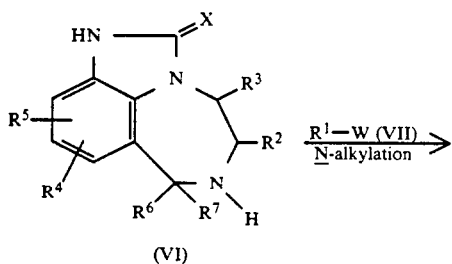

$\xrightarrow{R^1-W \ (VII)}_{\underline{N}\text{-alkylation}}$ (VI)

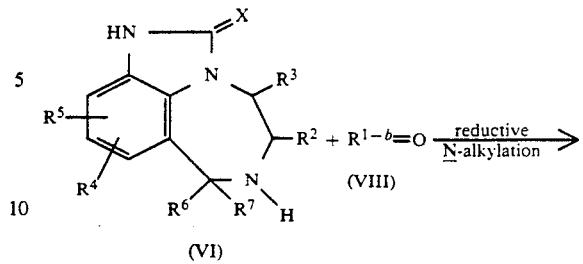

$+ R^{1-b}=O \xrightarrow{\text{reductive}}_{\underline{N}\text{-alkylation}}$ (VIII)

(VI)

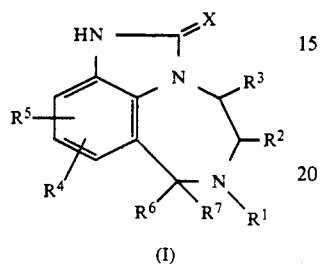

(I)

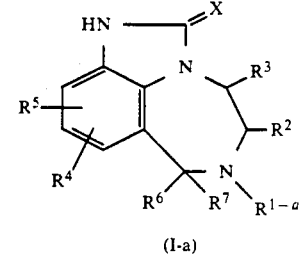

(I-a)

Said N-alkylation reaction may conveniently be conducted in a reaction-inert solvent such as, for example, an aromatic hydrocarbon, e.g., benzene, methylbenzene, dimethylbenzene and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g. N,N-dimethylformamide, N,N-dimethylacetamide, nitrobenzene, dimethyl sulfoxide, 1-methyl-2-pyrrolidinone, and the like, or a mixture of such solvents. The addition of an appropriate base such as, for example, an alkali metal carbonate or hydrogen carbonate, e.g. sodium carbonate, sodium hydrogen carbonate; sodium hydride or an organic base such as, for example, N,N-diethylethanamine or N-(1-methylethyl)-2-propanamine and the like may be utilized to pick up the acid which is liberated during the course of the reaction. In some circumstances the addition of an iodide salt, preferably an alkali metal iodide, e.g. potassium iodide, is appropriate. Somewhat elevated temperatures and stirring may enhance the rate of the reaction.

The compounds of formula (I) wherein $R^1$ is $C_{1-6}$alkyl optionally substituted with aryl; $C_{3-6}$cycloalkyl or a radical of formula (a-3) and the carbon atom of said $R^1$ radical adjacent to the nitrogen atom bearing said $R^1$ contains at least one hydrogen atom, said radicals being represented by $R^{1-a}$, and said compounds by formula (I-a), may also be prepared by the reductive N-alkylation of an intermediate of formula (VI) with a ketone or aldehyde of formula $R^{1-b}=O$ (VIII). In formula (VIII), $R^{1-b}$ represents a geminal bivalent radical derived from $R^{1-a}$—H wherein two geminal hydrogen atoms are replaced by =O.

Said reductive N-alkylation reaction may conveniently be carried out by catalytically hydrogenating the reactants in a suitable reaction-inert organic solvent according to art-known catalytic hydrogenation procedures. The reaction mixture may be stirred and/or heated in order to enhance the reaction rate. Suitable solvents are, for example, water; $C_{1-6}$alkanols, e.g. methanol, ethanol, 2-propanol and the like; ethers, e.g. 1,4-dioxane and the like; halogenated hydrocarbons, e.g. trichloromethane and the like; dipolar aprotic solvents, e.g. N,N-dimethylformamide, dimethyl sulfoxide and the like; esters, e.g. ethyl acetate and the like; or a mixture of such solvents. The term art-known catalytic hydrogenation procedures means that the reaction is carried out under a hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like. Alternatively, said reductive N-alkylation may also be performed following art-known reduction procedures by treating a stirred and, if desired, heated mixture of the reactants with a reducing agent such as, for example, sodium borohydride, sodium cyanoborohydride, formic acid or a salt thereof, in particular the ammonium salt thereof.

The compounds of formula (I) wherein X is S, said compounds being represented by formula (I-b-2), can be prepared by thionation of the compounds of formula (I) wherein X is O, said compounds represented by formula (I-b-1), with phosphorus pentasulfide in an appropriate reaction-inert solvent. Such solvents are for example, aromatic hydrocarbons, e.g. benzene, methylbenzene, dimethylbenzene, dipolar aprotic solvents, e.g. hexamethylphosphoric triamide (HMPA) and the like solvents.

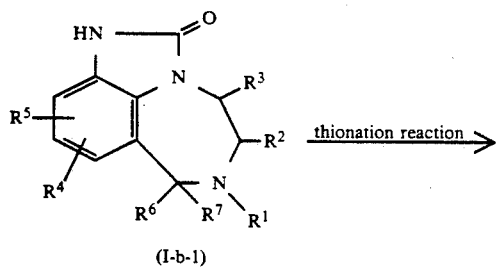

(I-b-1)

thionation reaction ⟹

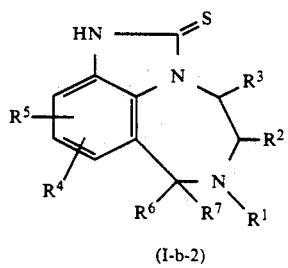

(I-b-2)

Based on the currently available test data, it appears that the compounds 6-allyl-4,5,6,7-tetrahydroimidazo[4,5,1-jk][1,4]benzodiazepin-2(1H)-one and (R)-4,5,6,7-tetrahydro-5-methyl-6-(2-propenyl)imidazo[4,5,1-jk][1,4]benzodiazepin-2(1H)-one have a disfavorable therapeutic index. However, these compounds of formula (I-b-2) are useful as intermediates for preparing the compounds of formula (I-b-2). This also applies for the compounds of formula (I-b-1) wherein $R^1$ is phenylmethyl or phenylethyl, $R^2$ is hydrogen or methyl and $R^3$, $R^4$, $R^5$, $R^6$ and $R^7$ are hydrogen, which also have a disfavorable therapeutic index according to the available test data.

The compounds of formula (I-b-2) may also be obtained by direct thiation of a tetrahydroimidazo[4,5,1-jk][1,4]benzodiazepine of formula (IX) with elemental sulfur at an elevated temperature.

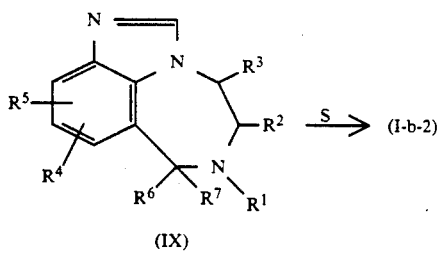

(IX)

Said reaction may conveniently be conducted without a solvent at a temperature above 200° C., more particularly a temperature in the range of 230° to 250° C.

The compounds of formula (I-b-2) may alternatively be prepared by the combined reduction-thiocarbonylation of a 9-nitrobenzodiazepine of formula (X) in the presence of an alkali metal sulfide or hydrogen sulfide, and carbon disulfide.

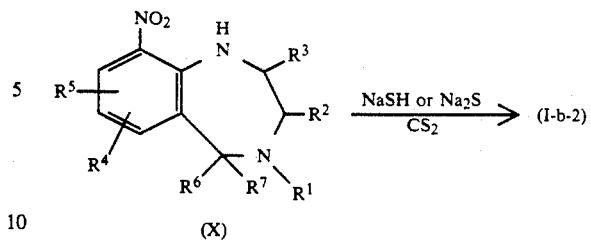

(X)

Said reduction-thiocarbonylation reaction may conveniently be conducted by stirring the reactants in a reaction-inert solvent, optionally at an elevated temperature.

The compounds of formula (I) can also be prepared by deprotecting the intermediates of formula (VI-P) followed by N-alkylation with a reagent of formula $R^1$—W (VII) as described for the preparation of (I) from (VI) and (VII).

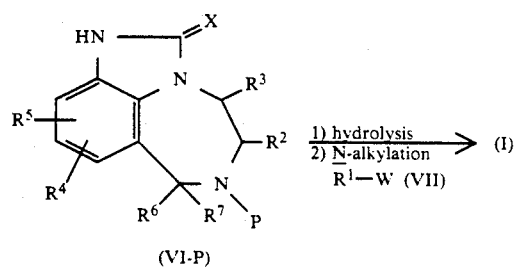

(VI-P)

P represents a suitable protective group like a $C_{1-4}$alkyloxycarbonyl, e.g., t.butyloxycarbonyl, benzyloxycarbonyl and the like, which can be removed by hydrolysis in an acid or alkaline medium.

In all of the foregoing and in the following preparations, the reaction products may be isolated from the reaction mixture and, if necessary, further purified according to methodologies generally known in the art.

A number of intermediates and starting materials in the foregoing preparations are known compounds which may be prepared according to art-known methodologies of preparing said or similar compounds and some intermediates are new. A number of such preparation methods will be described hereinafter in more detail.

The intermediates of formula (II) can generally be prepared from a 9-aminobenzodiazepine of formula (II-a) following N-alkylation reaction procedures such as described hereinabove for the preparation of the compounds of formula (I) and (I-a) from an intermediate of formula (VI) with an alkylating reagent (VII) or with an aldehyde or ketone of formula (VIII).

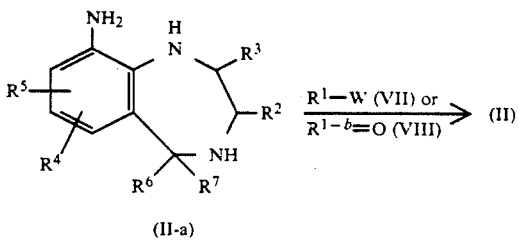

(II-a)

In order to simplify the following reaction schemes, the N-alkylated intermediates wherein $R^1$ is as defined under formula (I) and the N-unsubstituted intermediates (wherein $R^1$ is replaced by hydrogen) will be represented hereinafter by formulae wherein the N atom at the 4 position is substituted with $R^{1H}$, said $R^{1H}$ defining $R^1$ and hydrogen. In intermediates (II-H), (XI) and (XII) of scheme 1 hereinbelow, $R^{1H}$ also defines a radical of formula:

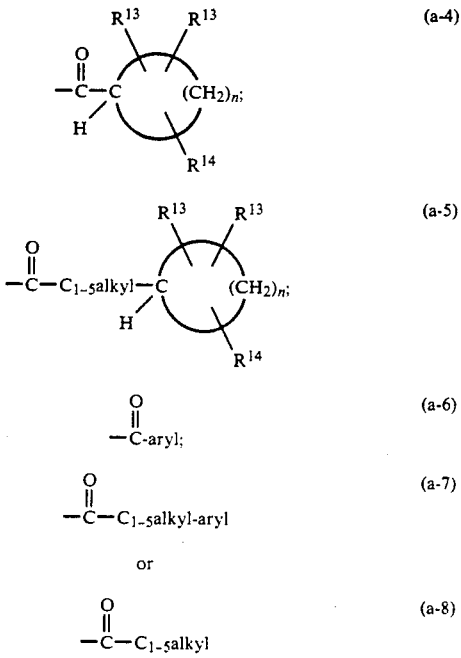

The latter amide intermediates can conveniently be prepared following art-known N-acylation procedures from corresponding intermediates wherein $R^{1H}$ is hydrogen and can be reduced to the corresponding N-alkylated intermediates with complex metal hydrides or hydrides as described under reaction step A of scheme 1. In all of the following reaction schemes, the intermediates wherein $R^{1H}$ is hydrogen can also be converted into intermediates wherein $R^{1H}$ is $R^1$ following the above described N-alkylation procedures with an alkylating reagent of formula $R^1-W$ (VII) or with an aldehyde or ketone of formula $R^{1-b}=O$ (VIII).

The intermediates of formula (II-H), said intermediates representing the intermediates of formula (II) and (II-a) can generally be prepared following the reaction steps shown in the reaction scheme 1 below.

dures (reaction step A). Said reduction may conveniently be conducted by treatment of said nitrobenzenes with a reducing agent such as, for example, a complex metal hydride, e.g. lithium aluminum hydride; a hydride, e.g. diborane, aluminum hydride and the like, in a reaction-inert solvent such as, for example, 1,1'-oxybisethane, tetrahydrofuran, 1,4-dioxane, 1,2-dimethoxyethane and the like, optionally in the presence of a cosolvent such as an aromatic hydrocarbon, e.g. benzene, methylbenzene and the like, and, if desired, at an elevated temperature. Alternatively, said reduction may also be accomplished by treatment of said nitrobenzene derivative with sodium dithionite, sodium sulfide, sodium hydrogen sulfide, titanium (III)chloride and the like reducing agents in a suitable solvent, in particular water. Said nitro-to-amine reduction can also be conducted following art-known catalytic hydro-genation procedures. For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture.

The 9-nitrobenzodiazepine (XI) in the above reaction scheme 1 can be prepared from the benzodiazepine (XII) following art-known nitration procedures (reaction step B). For example, the starting material may be nitrated by treatment with concentrated or fuming nitric acid in the presence of concentrated sulfuric acid and optionally in the presence of a cosolvent such as, for example, a halogenated hydro-carbon, e.g. dichloromethane, trichloromethane, tetrachloromethane and the like solvents. Alternatively, said nitration may in some instances also be accomplished by adding the nitrate salt of the starting material to concentrated sulfuric acid.

The intermediates of formula (II-H) wherein $R^6$ and $R^7$ are hydrogen, said intermediates being represented by (II-H-1) may be obtained following the reaction steps shown in reaction scheme 2 below. Reaction steps designated A and B are intended to refer back to the Scheme 1

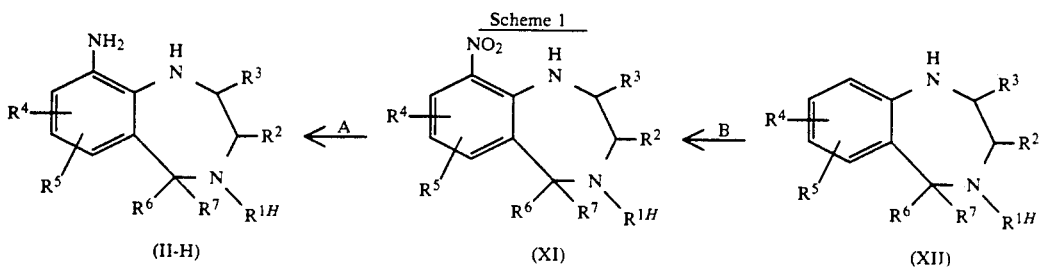

A: nitro-to-amine reduction (if $R^{1H}$ = acyl; also amide-to-amine reduction)
B: nitration The 9-aminobenzodiazepine (II-H) in the above reaction scheme may conveniently be prepared by reduction of the corresponding nitrobenzene derivative (XI) following art-known nitro-to-amine reduction proceanalogous reaction steps described in the previous reaction scheme.

The benzodiazepine derivatives (XIII), (XIV) and (XV) may be obtained from the corresponding aniline derivatives (XVI), (XVII) and (XVIII) (Reaction step C) by cyclization. Said cyclization reaction may be conducted by stirring, and, if desired, heating the starting material. Suitable solvents are, for example, aromatic hydrocarbons, e.g. benzene, methylbenzene, dimethylbenzene and the like, halogenated hydrocarbons, e.g. trichloromethane, tetrachloromethane, chlorobenzene and the like, ethers, e.g. tetrahydrofuran, 1,4-dioxane and the like, dipolar aprotic solvents e.g. N,N-dimethylformamide, N,N-dimethylacetamide, acetonitrile, dimethylsulfoxide, pyridine and the like. Bases which may be employed in said cyclization reaction are, for example, alkali metal or alkaline earth metal carbonates, hydrogen carbonates, hydroxides, oxides, amides, hydrides and the like. In some instances the addition to the reaction mixture of a iodide salt, preferably an alkali metal iodide, e.g. potassium iodide, may be advantageous.

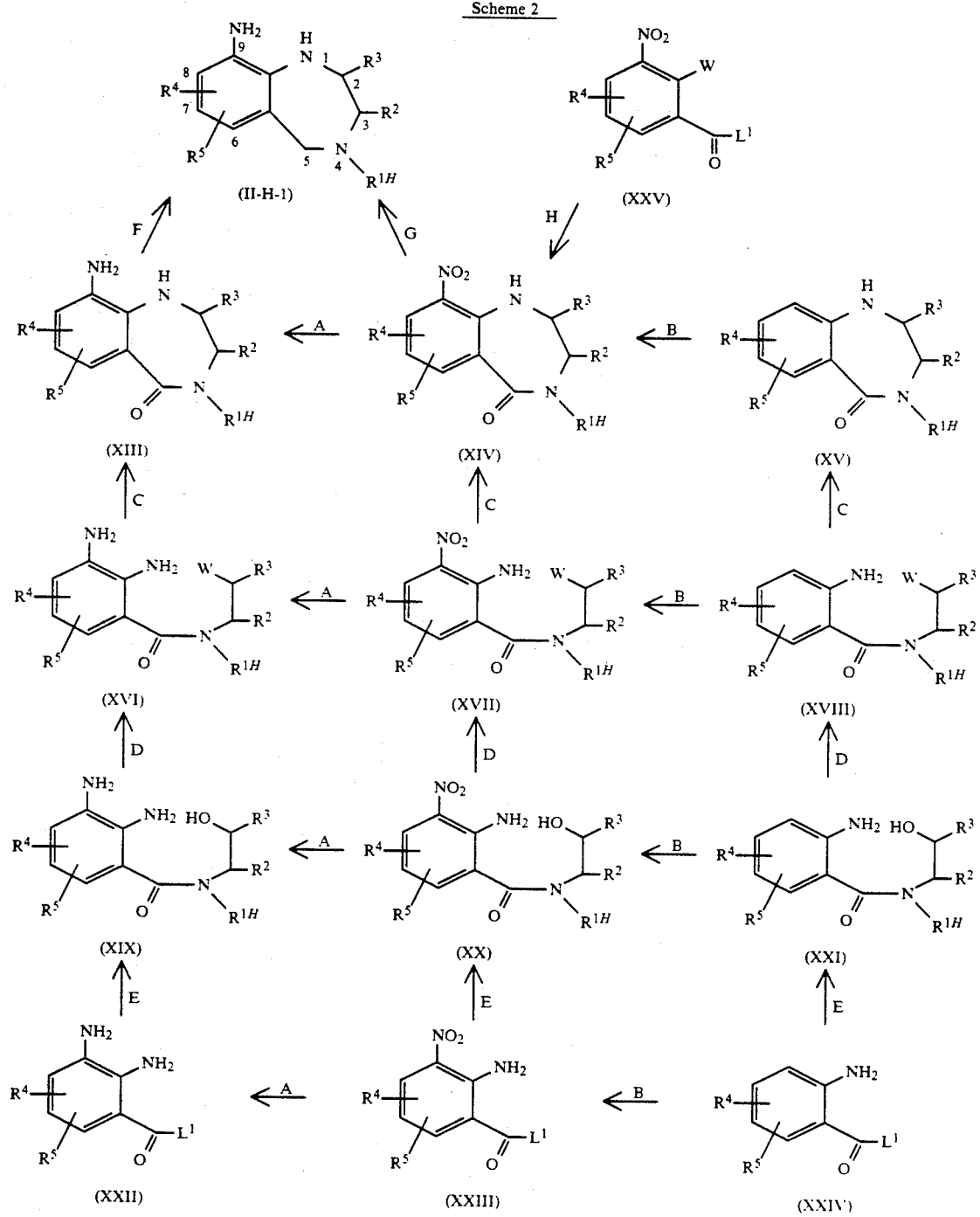

Scheme 2

C: cyclization
D: —OH to —W activation
E: N-acylation reaction; $R^{1H}NH-CH(R^2)-CH(R^3)OH$ (XXVII)

-continued
Scheme 2

F: amide-to-amide reduction
G: (nitro-to-amino) and (amide-to-amine) reduction
H: cyclization; $R^{1H}-NH-CH(R^2)-CH(R^3)-NH_2$ (XXVI)

The aniline derivatives (XVI), (XVII) and (XVIII), wherein W is a reactive leaving group as defined hereinbefore, may be prepared from the corresponding alkanols by treatment with a halogenating reagent such as, for example, thionyl chloride, phosphoryl chloride, phosphorous trichloride and the like; or by treatment with a sulfonylating reagent, e.g. methanesulfonyl chloride, 4-methylbenzenesulfonyl chloride and the like (Reaction step D).

Said alkanols (XIX), (XX) and (XXI) may be prepared by N-acylating an ethanolamine of formula $R^{1H}NH-CH(R^2)-CH(R^3)-OH$ (XXVII) with an appropriately substituted 2-aminobenzoic acid derivative of formula (XXII), (XXIII) or (XXIV) wherein $L^1$ represents hydroxy or a leaving group such as, for example, halo, e.g. chloro or bromo; alkylcarbonyloxy, e.g. acetyl; alkyloxy, e.g. methoxy, ethoxy and the like; or imidazolyl and the like leaving groups. Said N-acylation reaction (reaction step E) may be carried out by stirring the reactants in a reaction-inert solvent, optionally at an elevated temperature. In those instances where $L^1$ represents hydroxy, said N-acylation reaction may also be carried out by treating the reactants with reagents capable of forming amides such as, for example, N,N-dicyclohexylcarbodiimide (DCC) optionally in the presence of a catalyst such as hydroxybenzotriazole (HOBT) or 4-dimethylaminopyridine (DMAP); 2-chloro-1-methylpyridinium iodide, 1,1'-carbonylbis[1H-imidazole], 1,1'-sulfonylbis[1H-imidazole] and the like reagents. Suitable solvents are halogenated hydrocarbons, e.g. dichloromethane, trichloromethane and the like, ethers, e.g. tetrahydrofuran, 1,4-dioxane and the like, dipolar aprotic solvents, e.g. N,N-dimethylformamide, N,N-dimethylacetamide, pyridine and the like; or mixtures of such solvents.

The intermediates of formula (II-H-1) can be prepared from a 9-amino- or a 9-nitrobenzodiazepin-5-one of formula (XIII) or (XIV) by reduction with a complex metal hydride e.g. lithium aluminum hydride and the like in a suitable reaction-inert solvent such as, for example, 1,2-dimethoxyethane, 1,1'-oxybis(2-methoxyethane), 2,5,8,11-tetraoxadodecane, methoxybenzene and the like solvents (Reaction steps F and G). In order to enhance the rate of said reduction reaction it may be advantageous to employ an excess of the reducing reagent and to conduct said reaction at an enhanced temperature of the reaction mixture, in particular the reflux temperature of the reaction mixture.

The intermediates of formula (XIV) can alternatively be obtained from an appropriately substituted nitrobenzene (XXV) by a condensation reaction (reaction step H) with a diamino reagent $R^{1H}NH-CH(R^2)-CH(R^3)-NH_2$ of formula (XXVI) in a suitable reaction-inert solvent such as, for example, an alkanol, e.g. methanol, ethanol, 2-propanol, 1-butanol and the like; an aromatic hydrocarbon, e.g. benzene, methylbenzene, dimethylbenzene and the like; a halogenated hydrocarbon, e.g. trichloromethane, tetrachloromethane and the like; an ether, e.g. tetrahydofuran, 1,4-dioxane, 1,1'-oxybisbutane, 1,1'-oxybis(2-methoxyethane) and the like; a ketone, e.g. 2-propanone. 4-methyl-2-pentanone and the like; a dipolar aprotic solvent, e.g. N,N-dimethylformamide, N,N-dimethylacetamide, dimethyl sulfoxide and the like; or a mixture of such solvents. It may be appropriate to add a base such as an alkali metal or an alkaline earth metal carbonate, e.g. sodium carbonate, sodium hydrogen carbonate and the like, to the reaction mixture. Said condensation reaction can conveniently be conducted at an elevated temperature, in particular at the reflux temperature of the reaction mixture.

The intermediates of formula (II-H-1) wherein $R^3$ is hydrogen, said intermediates being represented by formula:

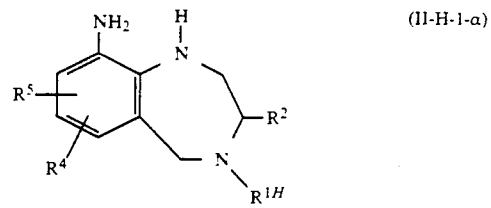

(II-H-1-a)

can also be prepared from a benzodiazepinedione of formula

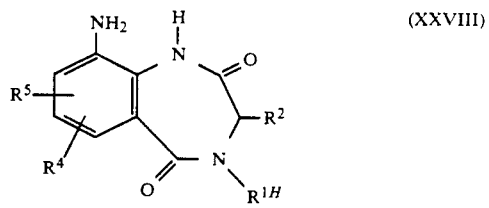

(XXVIII)

following the reduction procedures as described hereinabove for converting intermediate (XIII) into intermediate (II-H-1) (reaction step F). The preparation of the intermediates of formula (XXVIII) may generally be conducted following the reaction pathways described in scheme 3 hereinbelow.

In all of the following reaction schemes. those intermediates wherein $R^3$ is hydrogen, are designated by appending the suffix -α to their numerical reference, and the intermediates wherein $R^6$ and $R^7$ are hydrogen, are designated by appending the suffix -1- to their numerical reference.

Scheme 3

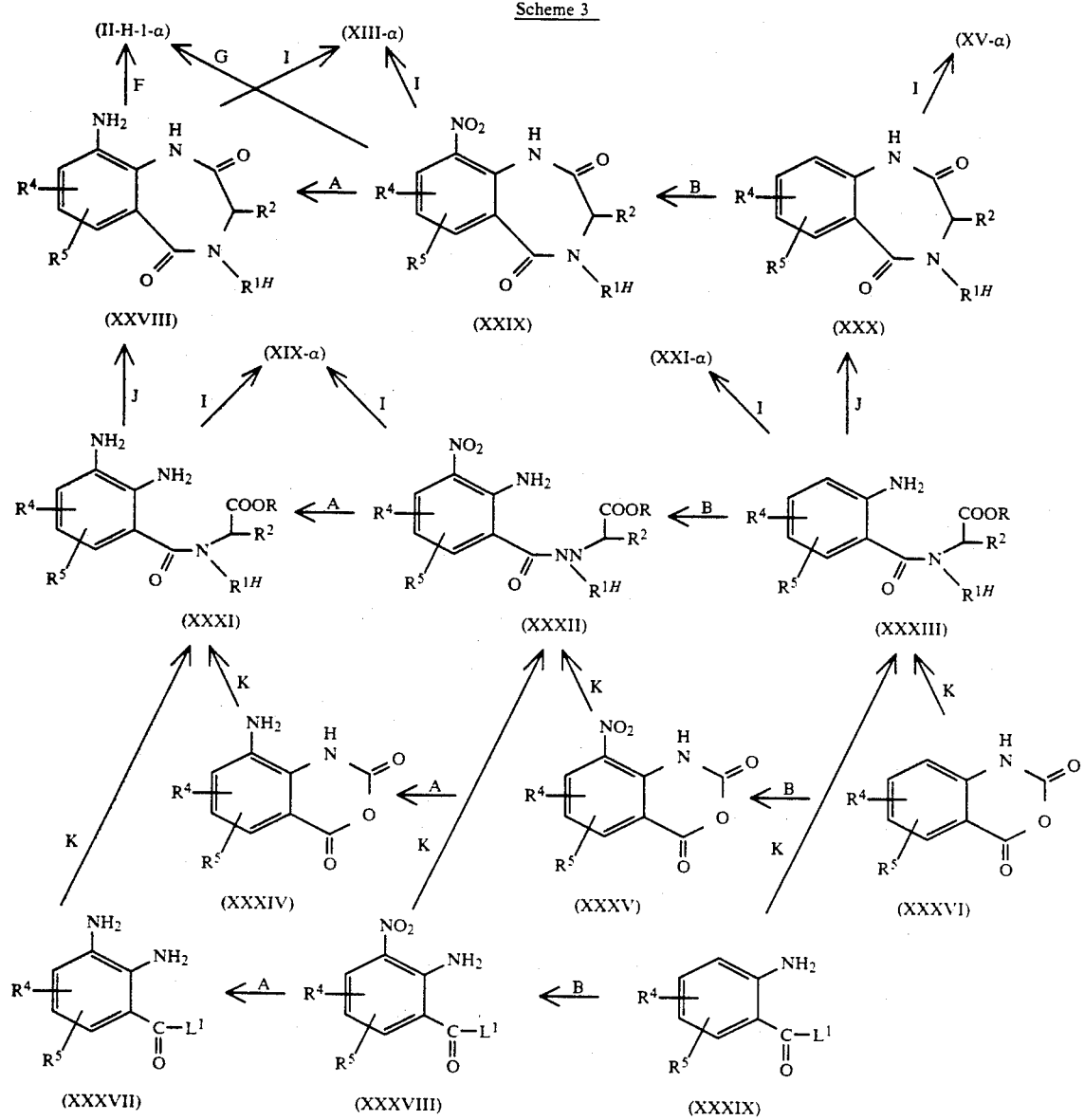

I: (nitro-to-amino) and/or aliphatic amide-to-amine and/or ester reduction
J: cyclization to benzodiazepinedione
K: N-acylation of $R^{1H}NH-CH(R^2)-COOR$ (XL)

In a number of the intermediates shown in scheme 3, for example in (XXVIII), (XXIX), (XXX), (XXXI), (XXXII) and (XXXIII) it is further possible to selectively reduce functional groups such as the nitro group, the ester group and/or the aliphatic amide group, in the presence of the aromatic amide group (reaction step I). Said selective reduction may be carried out by treatment of the appropriate starting material with a complex metal hydride such as, for example, lithium aluminum hydride in a reaction-inert solvent such as, for example, tetrahydrofuran, 1,4-dioxane and the like. Alternatively, said selective reduction may also be performed by treatment of the appropriate starting material with sodium bis(2-methoxyethoxy) aluminum hydride, or with sodium borohydride in the presence of a suitable metal salt such as, for example, titanium(IV)chloride, calcium chloride, cerium(III) chloride, aluminum chloride, zirconium(IV)chloride and the like metal salts, in a reaction-inert solvent, in particular an ether.

The benzodiazepinediones (XXVIII) and (XXX) in scheme 3 can be obtained by cyclizing (reaction step J) the corresponding acyclic intermediates of formula (XXXI) and (XXXIII) wherein R represents a group such as $C_{1-6}$alkyl or aryl, a) by heating without a solvent under an inert atmosphere, optionally under reduced pressure;

b) by treating with a bifunctional catalyst such as, for example, acetic acid, 2-hydroxypyridine, pyrazole, 1,2,4-triazole and the like, in a reaction-inert solvent such as, for example, an aromatic hydrocarbon, e.g. methylbenzene, dimethylbenzene and the like, optionally at an elevated temperature; or c) by hydrolyzing the ester and subsequently treating the corresponding carboxylic acid (R=H) with an appropriate acid, such as, for example, a hydrohalic acid, e.g. hydrochloric acid; sulfuric acid, phosphoric acid and the like acids; or with a halogenating reagent such as, for example, thionyl chloride and the like.

Said intermediates in turn, can be prepared from an appropriately protected amino acid of formula $R^{1H}$—NH—CH($R^2$)—COOR (XL) wherein R is $C_{1-6}$alkyl or aryl, by a N-acylation reaction (reaction step K) with an appropriately substituted isatoic anhydride derivative or an appropriate 2-aminobenzoic acid derivative, by stirring the reactants at reflux temperature in a reaction-inert solvent such as, for example, trichloromethane, pyridine and the like solvents.

The intermediates of formula (II-H), wherein $R^3$ is hydrogen, said intermediates being represented by (II-H-α) may be prepared from benzodiazepin-2-one derivatives following the procedures described in scheme 4.

Reaction steps A, B, I and J are intended to refer back to the analogous reaction steps described hereinbefore.

The intermediates of formula (XLIV), (XLV) and (XLVI) can be prepared from an appropriately protected amino acid of formula $R^{1H}$—NH—CH($R^2$)—COOR (XL) wherein R is $C_{1-6}$alkyl or aryl, by a N-alkylation reaction (reaction step L) with an intermediate of formula (XLVII), (XLVIII) and (IL) in a reaction inert solvent.

The intermediates of formula (II-H) wherein $R^6$ and $R^7$ are hydrogen and $R^3$ is $C_{1-6}$alkyl, said radical being represented by $R^{3-a}$ and said intermediates by formula

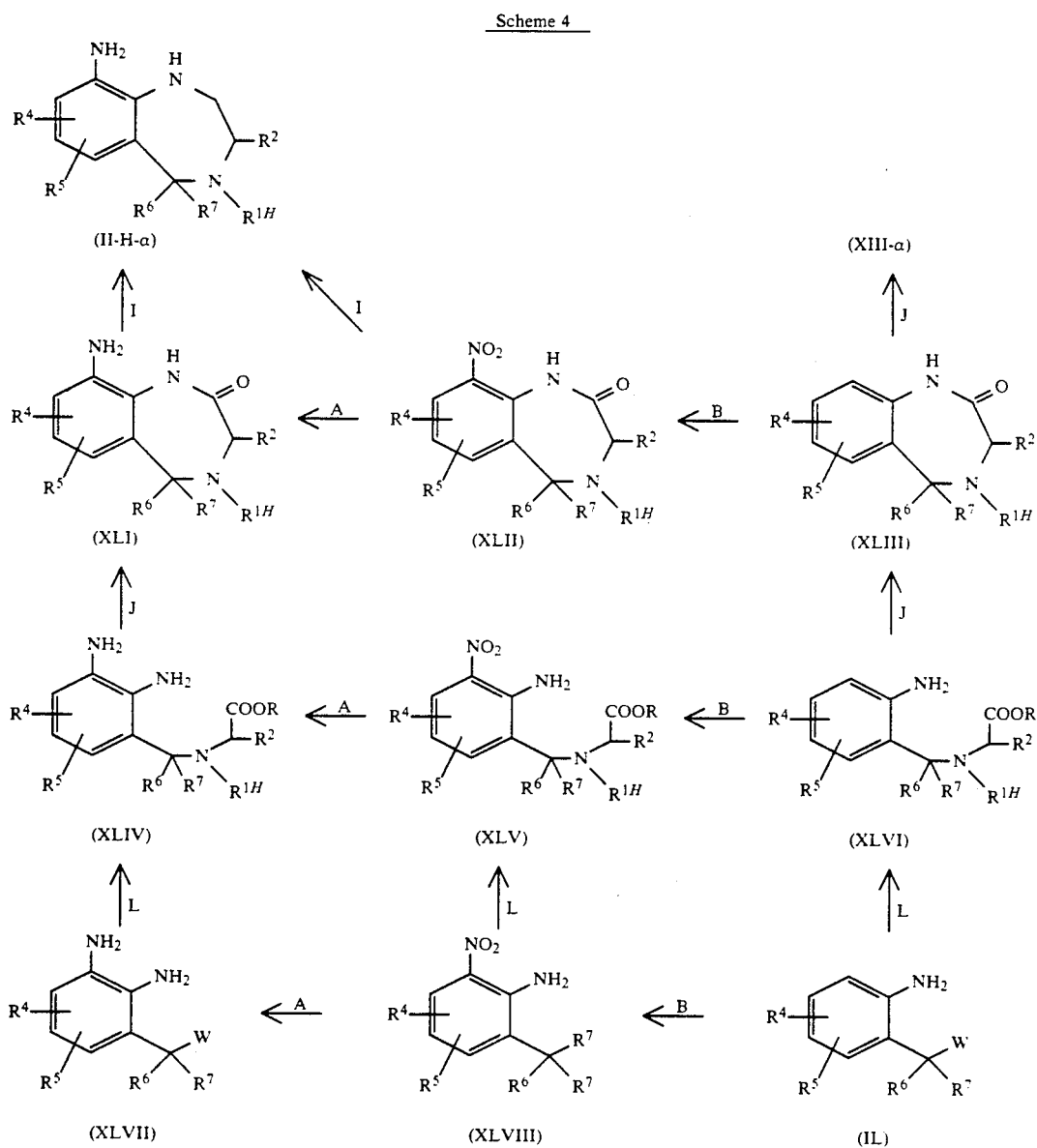

Scheme 4

L: N-alkylation: $R^{1H}$NH—CH($R^2$)—COOR (XL)

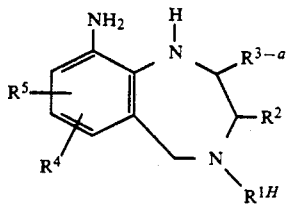
(II-H-β)

can be prepared by the reduction of an amine (XIII-b) or an imine (L), following the reduction procedures as described hereinabove for the preparation of (II-H-1) from (XIII) or (XIV).

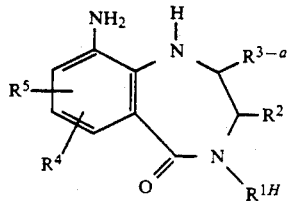
(XIII-b)

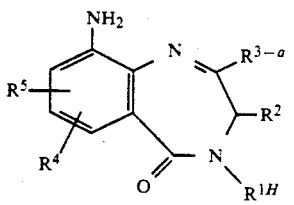
(L)

The imine (L) can be prepared by reducing a nitro derivative (LI) in the presence of hydrogen and a suitable metal catalyst such as, for example, palladium-on-charcoal, platinum oxide and the like catalysts. The ketone of formula (LI) in turn can be prepared from a 2-amino-3-nitrobenzoic acid or a functional derivative thereof (XXIII) and an α-aminoketone (LII) following art-known N-acylation procedures.

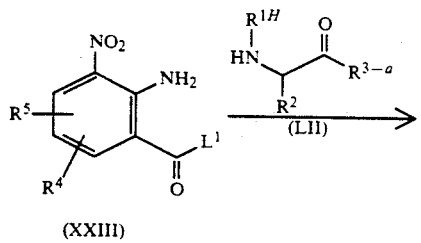

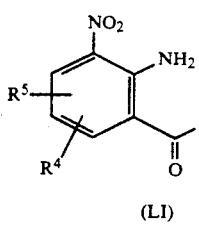
(LI)

The intermediates of formula (IV) can generally be prepared from the compounds of formula (I-b-1) by reacting with a halogenating reagent such as, for example, phosphoryl chloride, phosphorous trichloride, phosphorous tribromide, thionyl chloride, and the like reagents, optionally at an elevated temperature, in particular the reflux temperature of the reaction mixture, and optionally in the presence of a base such as, for example, sodium carbonate, sodium hydrogen carbonate, potassium carbonate and the like. The reaction can be conducted in an excess of the halogenating reagent as solvent and optionally a reaction-inert solvent such as an aromatic hydrocarbon or an ether may be used as well. Or alternatively, the compounds of formula (I-b-1) can be reacted with an acid anhydride, e.g. trifluoroacetic anhydride to form an O-acylated intermediate which can be further converted with a hydrogen halide, such as hydrogen chloride, into intermediates of formula (IV). The reaction can be carried out in a reaction-inert solvent like an aromatic hydrocarbon or an ether in the presence of a base, such as, for example, a pyridine, e.g. a picoline, 2,6-lutidine and the like.

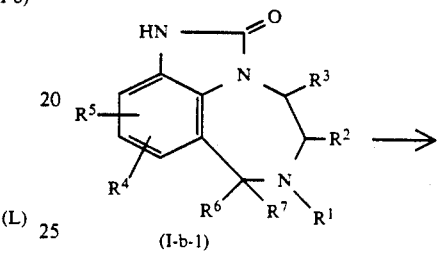
(I-b-1)

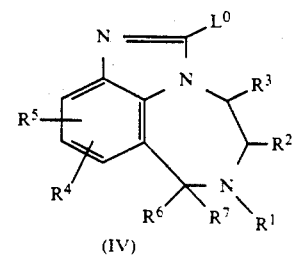
(IV)

The intermediates of formula (VI) wherein $R^2$, $R^3$, $R^4$, $R^5$, $R^6$, $R^7$ and X are as defined under formula (I) are novel and can be prepared from intermediates of formula (II-a) following the condensation reaction with a reagent of formula L-C(=X)-L (III) as described hereinbefore for the preparation of the compounds of formula (I) from the intermediates of formula (II).

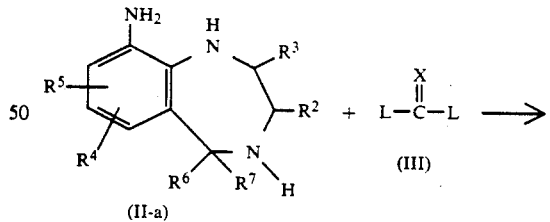
(II-a)  (III)

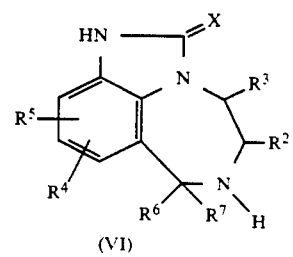
(VI)

The intermediates of formula (VI) can also be obtained from a benzylated compound of formula (I-c) following art-known hydrogenolysis procedures.

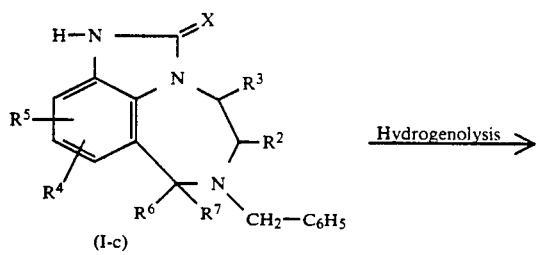

(I-c)

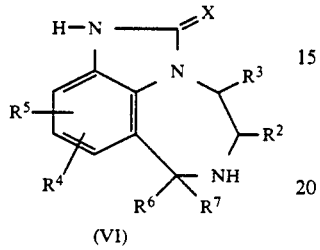

(VI)

Said debenzylation reaction can be accomplished by stirring a compound of formula (I-c) in an appropriate reaction-inert solvent in the presence of a suitable metal catalyst and under a hydrogen atmosphere. Appropriate solvents are, for example, alkanols, e.g. methanol, ethanol and the like; carboxylic esters, e.g. ethyl acetate; carboxylic acids, e.g. acetic acid, propanoic acid and the like. As examples of suitable metal catalysts there may be mentioned palladium-on-charcoal, platinum-on-charcoal and the like catalysts. In order to prevent the further hydrogenation of the starting material and/or the reaction product it may be appropriate to add a catalyst-poison to the reaction mixture such as, for example thiophene.

The intermediates of formula (VI) wherein $R^6$ and/or $R^7$ are methyl, said intermediates being represented by formula (VI-a) and (VI-b) can be prepared from 9-aminobenzodiazepin-5-ones of formula (XIII-a) as shown in the next reaction scheme.

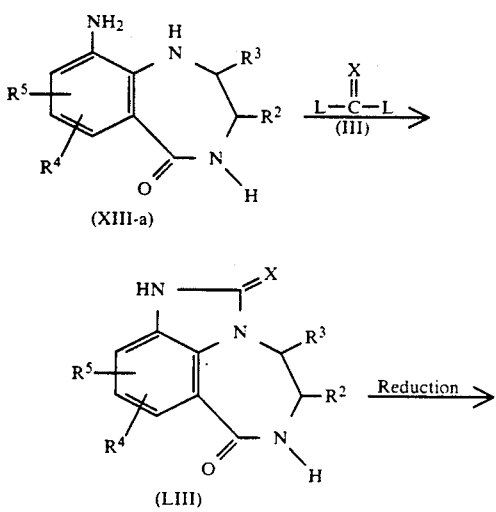

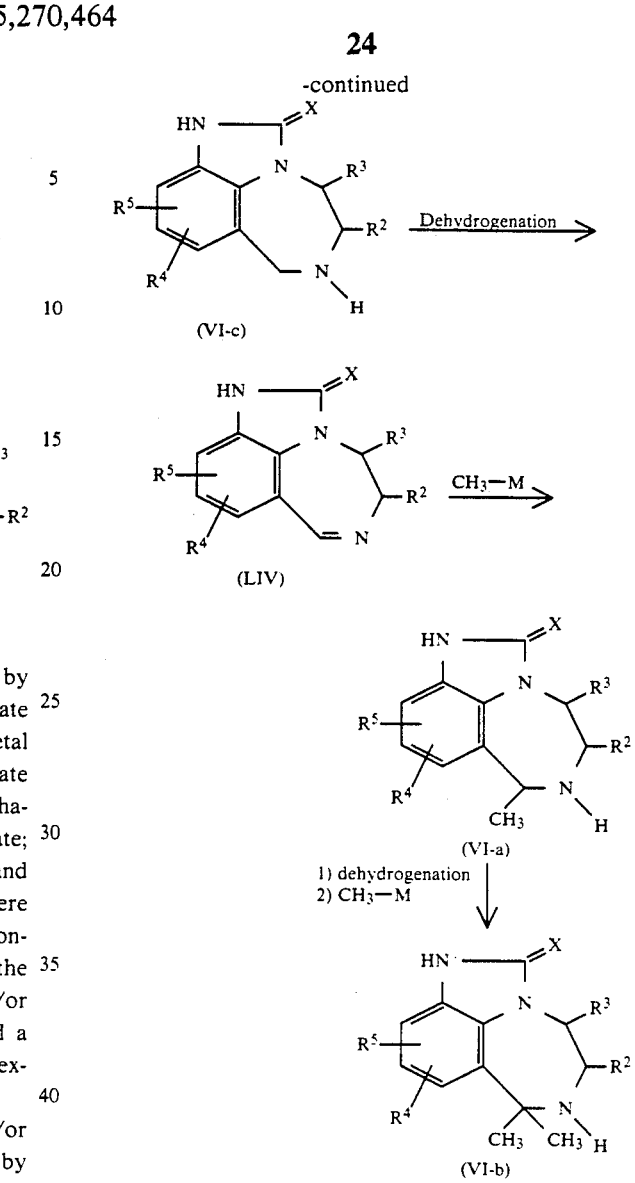

The benzodiazepin-7-ones of formula (LIII) can be prepared from an intermediate of formula (XIII-a) following the condensation reaction with a reagent of formula L—C(=X)—L (III) as described for the preparation of (I) from (II) and (III). The benzodiazepin-7-ones (LIII) can be reduced to benzodiazepines of formula (VI), wherein $R^6$ and $R^7$ are both hydrogen, said intermediates being represented by formula (VI-c), with a complex metal hydride, e.g. lithium aluminum hydride and the like in a suitable reaction-inert solvent such as, for example, 1,2-dimethoxyethane, 1,1'-oxybis-(2-methoxyethane),2,5,8,11-tetraoxadodecane, methoxybenzene and the like solvents. In order to enhance the rate of said reduction reaction, it may be advantageous to employ an excess of the reducing reagent and to conduct said reaction at an enhanced temperature, in particular the reflux temperature of the reaction mixture.

The thus obtained benzodiazepines of formula (VI-c) can be dehydrogenated to intermediates of formula (LIV). Said dehydrogenation can be carried out by oxidation of (VI-c) with permanganate or with manganese(IV)oxide in a suitable reaction-inert solvent such as, for example, water, an alcohol, e.g. methanol, ethanol and the like, an ether, e.g. 1,1'-oxybisethane, tetrahydrofuran and the like or a mixture of such solvents. Or alternatively, the imine (LIV) may also be obtained by reaction with nickel, platinum or chromium catalysts; or in the presence of easily reducible substances such as sulfur, amyldisulfide, selenium or sodium amide in liquid ammonia.

The benzodiazepines of formula (VI) wherein $R^7$ is hydrogen and $R^6$ is methyl, said intermediates being represented by formula (VI-a), can be prepared from intermediates of formula (LIV) by reaction with organometallic compounds of formula $CH_3$-M, wherein M represents a metal group such as, for example, lithium, halo magnesium, copper lithium and the like, in a reaction-inert solvent like an ether, e.g. tetrahydrofuran, 1,1'-oxybisethane, 1,2-dimethoxyethane and the like; a hydrocarbon, e.g. hexane, benzene, methylbenzene and the like, or a mixture thereof.

The benzodiazepines of formula (VI), wherein $R^6$ and $R^7$ are both methyl, said intermediates being represented by formula (VI-b), can be obtained in a similar way. Dehydrogenation of (VI-a) yields an imine, which can be converted to the 7-dimethyl-benzodiazepine (VI-b) with organometallic compounds of formula $CH_3$-M, following the same procedures as described hereinabove for the preparation of (VI-a) from (VI-c).

The intermediates of formula (VI), wherein X is S, said intermediates being represented by formula (VI-b-2), may be prepared by thionation of an intermediate of formula (VI-b-1) following the procedures described hereinabove for the preparation of the compounds of formula (I-b-2) from (I-b-1).

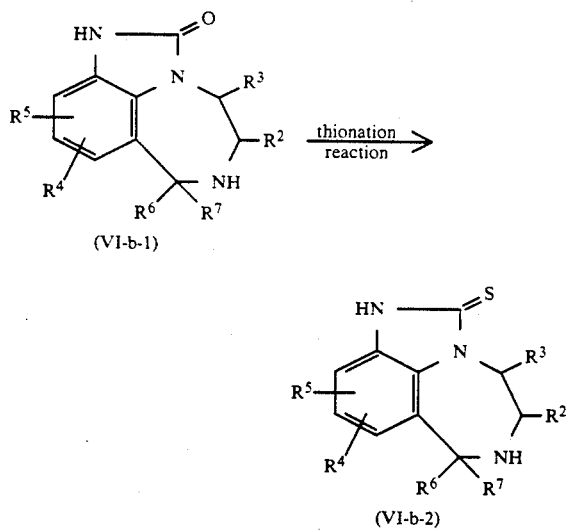

(VI-b-1)

(VI-b-2)

The intermediates of formula (XI) wherein $R^{1H}$ and $R^7$ are both hydrogen, said intermediates being represented by (XI-a) can also be obtained by reacting an appropriately substituted nitrobenzene (LV) and a diamino reagent of formula (LVI). Herein Y is either hydrogen or a removable protective group such as, for example, $C_{1-6}$alkylcarbonyl, e.g. acetyl, trichloroacetyl and the like, a benzyl group, a $C_{1-6}$alkyloxycarbonyl group, e.g. 1,1-dimethylethyloxycarbonyl, and the like groups commonly used to protect an amino group.

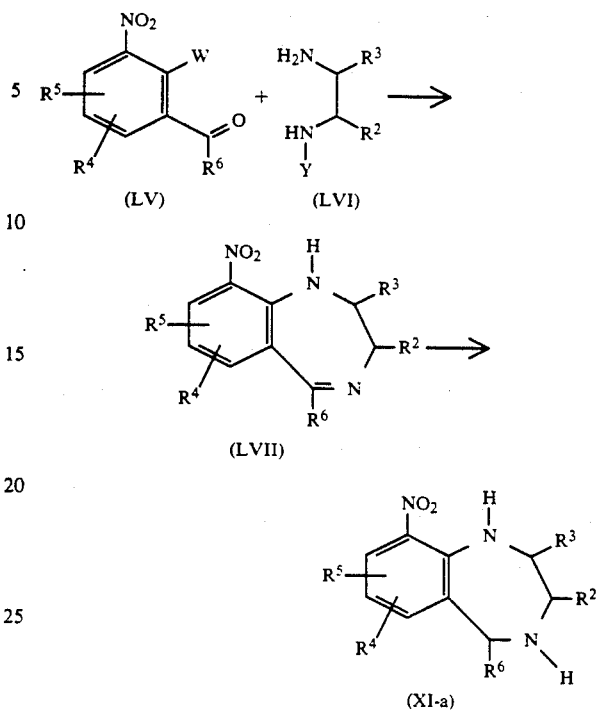

Said reaction may conveniently be conducted by condensing the diamino reagent of formula (LVI) with the nitrobenzene of formula (LV), optionally removing the protective group by alkaline or acid hydrolysis or by catalytic hydrogenation and reducing the thus obtained intermediate (LVII). Said condensation reaction can conveniently be conducted in a suitable reaction-inert solvent such as, for example, an alkanol, e.g. methanol, ethanol, 2-propanol, 1-butanol and the like; an aromatic hydrocarbon, e.g. benzene, methylbenzene, dimethylbenzene and the like; a halogenated hydrocarbon, e.g. trichloromethane, tetrachloromethane and the like; an ether, e.g. tetrahydrofuran, 1,4-dioxane, 1,1'-oxybisbutane, 1,1'-oxy(2-methoxyethane) and the like; a ketone, e.g. 2-propanone, 4-methyl-2-pentanone and the like; a dipolar aprotic solvent, e.g. N,N-dimethylformamide, N,N-dimethylacetamide, dimethyl sulfoxide and the like; or a mixture of such solvents. It may be appropriate to add a base such as an alkali metal or earth alkaline metal carbonate, e.g. sodium carbonate, sodium hydrogen carbonate and the like, to the reaction mixture. Said condensation reaction can conveniently be conducted at an elevated temperature, in particular at the reflux temperature of the reaction mixture. Said reductions in the above procedure may conveniently be conducted by reaching the intermediate imines with a suitable reductive reagent such as, for example, sodium borohydride, sodium cyanoborohydride and the like reductive reagents.

The intermediates of formula (XI-a) wherein $R^3$ and $R^7$ are both H, said intermediates being represented by formula (XI-a-α), can also be prepared by reacting a substituted nitrobenzene (LV) with an amide of formula (LVIII). The thus obtained intermediates can be further reduced to intermediates of formula (XI-a-α) following procedures described hereinabove for the preparation of (XI-a).

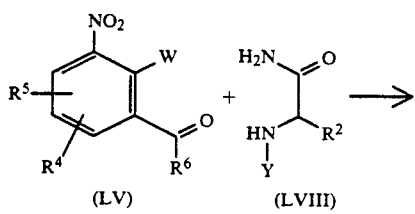

(LV)  (LVIII)

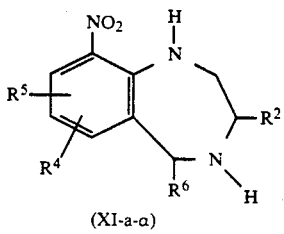

(XI-a-α)

The compounds of formula (I) and the above described intermediates can also be converted into each other following art-known procedures of functional group transformation. Some examples of such procedures are cited hereinafter. The compounds of formula (I) wherein $R^4$ or $R^5$ is a nitro group can be obtained following art-known nitration procedures, as described hereinbefore (reaction step B of scheme 1). The compounds of formula (I) wherein $R^4$ or $R^5$ is a nitro substituent can be converted into the corresponding amines by stirring and, if desired, heating the starting nitro compounds in hydrazine hydrate in the presence of a catalyst like Raney-nickel or in a hydrogen containing medium in the presence of an appropriate catalyst such as, for example, platinum-on-charcoal, Raney-nickel and the like catalysts or following other methods as described hereinbefore (reaction step A of scheme 1). Suitable solvents are, for example, methanol, ethanol and the like. Amino groups may be alkylated or acylated following art-known procedures such as, for example, N-alkylation, N-acylation, reductive N-alkylation and the like methods. The compounds of formula (I) wherein $R^4$ or $R^5$ is a halo group can be obtained by halogenation of the corresponding compounds wherein $R^4$ or $R^5$ is hydrogen in a suitable reaction-inert solvent such as carbondisulfide, dichloromethane, trichloromethane and the like. Suitable halogenating reagents are for example, N-bromosuccinimide, chlorine, bromine and the like. In order to prevent side reactions, other reactive functionalities may be protected. Suitable protective groups are for example alkyloxycarbonyl groups like t-butyloxycarbonyl, benzyloxycarbonyl and the like. The compounds of formula (I) wherein $R^4$ or $R^5$ is halo may be converted into compounds wherein $R^4$ or $R^5$ is hydrogen following art-known hydrogenolysis procedures, e.g. by stirring and, if desired, heating the starting compounds in a suitable reaction-inert solvent in the presence of hydrogen and an appropriate catalyst such as, for example, palladium-on-charcoal and the like catalysts.

In all of the foregoing reaction schemes, the chemical designation of the intermediates defines the mixture of all possible stereochemically isomeric forms; mixtures of a number of possible stereochemically isomeric forms such as, for example, diastereomeric mixtures, enantiomeric mixtures, e.g. racemates and enriched enantiomeric mixtures; and the enantiomerically pure isomeric forms of the basic molecular structure.

Stereochemically isomeric forms of the intermediates described in the foregoing reaction schemes and of the compounds of formula (I) may be obtained by the application of art-known procedures. For example, diastereoisomers may be separated by physical separation methods such as destillation, selective crystallization, chromatographic techniques, e.g. counter current distribution, liquid chromatography and the like techniques. Pure enantiomers may be obtained by separating the corresponding racemates for example, by the selective crystallization of their diastereomeric salts with optically active resolving agents, chromatography of diastereomeric derivates, chromatography of the racemate over a chiral stationary phase and the like techniques. Alternatively, enantiomerically pure forms can conviently be obtained from the enantiomerically pure isomeric forms of the appropriate starting materials, provided that the subsequent reactions occur stereospecifically. Particularly interesting enantiomerically pure starting materials for use in the foregoing reaction schemes are aminoacids and/or substituted derivatives thereof, having the formula $R^{1H}NH\text{---}CH(R^2)\text{---}COOR$ (XL), the corresponding aminoalkanols $R^{1H}NH\text{---}CH(R^2)\text{---}CH(R^3)OH$ (XXVII) and diamino reagents $R^{1H}NH\text{---}CH(R^2)\text{---}CH(R^3)\text{---}NH_2$(XXVI).

The compounds of formula (I) show antiretroviral properties. Until recently, retroviruses were considered to be the pathogenic agents in a number of non-human warm-blooded animal diseases only, unlike viruses which have been known for quite some time to be the cause of a large number of diseases in warm-blooded animals and humans alike. However, since it has been established that a retrovirus, Human Immunodeficiency Virus (HIV), also known as LAV, HTLV-III or ARV, is the etiological agent of Acquired Immune Deficiency Syndrome (AIDS) in humans, retroviral infections and the treatment of subjects suffering therefrom have received the utmost attention. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers, rather than as a direct result of HIV infections. Other conditions associated with HIV infection include thrombo-cytopaenia, Kapos's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC). The antiretroviral and especially the anti-HIV properties of the compounds of formula (I) suggest said compounds to be useful antiretroviral chemotherapeutical agents for the prophylaxis or treatment of warm-blooded animals suffering from viral infections, more particularly for the treatment of humans infected by HIV virus.

Due to their antiretroviral properties, the compounds of formula (I), their pharmaceutically acceptable salts and the stereochemically isomeric forms thereof, are useful in the treatment of warm-blooded animals infected with retroviruses or for the prophylaxis of said warm-blooded animals. The compounds of the present invention may be especially useful in the treatment of warm-blooded animals infected with (retroviruses whose existence is mediated by, or depends upon, the enzyme reverse transcriptase), because these compounds inhibit the enzyme reverse transcriptase.

Examples of human retroviral infections include HIV and HTLV-I (human T-lymphotropic virus type I), causing leukemia and lymphoma. As an example of non-human animal retroviral infection there may be mentioned FeLV (feline leukemia virus) which causes leukemia and immunodeficiency. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

In view of their antiretroviral activity, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for precutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating retroviral diseases in warm-blooded animals suffering from said retroviral diseases by administering an effective antiretroviral amount of a compound of formula (I), a pharmaceutically acceptable acid addition salt or a steroisomeric form thereof. Those of skill in the treatment of viral diseases could easily determine the effective antiviral amount from the test results presented herein. In general it is contemplated that an effective amount would be from 0.1 mg/kg to 200 mg/kg body weight, and in particular from 1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The following examples are intended to illustrate and not to limit the invention in all its aspects. Unless otherwise stated, all parts therein are by weight.

EXPERIMENTAL PART

A.

Preparation of the intermediates

EXAMPLE 1 a) A mixture of 11.7 parts of methyl 2-bromo-3-nitrobenzoate, 8.1 parts of 1,2-ethanediamine monohydrate and 40 parts of 1-butanol was stirred for ½ hour at reflux temperature. The reaction mixture was evaporated and the residue was diluted with 50 parts of water. The precipitate was filtered off and washed with water and 2-propanol. It was then recrystallized from 2-methoxyethanol, yielding 6.5 parts of 2,3,4,5-tetrahydro-9-nitro-1H-1,4-benzodiazepin-5-one; mp. 191°-195° C. (interm. 1)

b) To a mixture of 6.3 parts of intermediate 1 in 60 parts of N,N-dimethylformamide there were added 3.7 parts of 2-methyl-2-propanol potassium salt and, after stirring for 15 min at 50° C., 4.2 parts of chloromethylbenzene. Stirring at 50° C. was continued for 1 hour. The reaction mixture was evaporated and the residue was diluted with 50 parts of water. The product was extracted with trichloromethane (3×75 parts) and the combined extracts were dried, filtered and evaporated. The residue was purified by column chromatography (silica gel; CHCl$_3$/C$_2$H$_5$OH 98:2). The eluent of the desired fraction was evaporated and the residue was crystallized from 2-propanol. The product was filtered off and dried, yielding 3.3 parts of 4-(phenylmethyl)-2,3,4,5-tetrahydro-9-nitro-1H-1,4-benzodizepin-5-one; mp. 129°-132° C. (interm. 2).

EXAMPLE 2 a) To a stirred suspension of 414 parts of 2-bromo-3-nitrobenzoic acid in 653 parts of methylbenzene there were added 440 parts of thionyl chloride. The whole was refluxed for 6 hours, cooled and left overnight. The reaction mixture was treated with activated charcoal, filtered over diatomaceous earth and evaporated. The residual oil was triturated with 396 parts of hexane (2×). The product was filtered off, washed with hexane and dried, yielding 363 parts (81.7%) of 2-bromo-3-nitrobenzoyl chloride (interm. 3).

b) A mixture of 14.9 parts of intermediate 3; 9.07 parts of 2,3-butanediamine dihydrochloride, 17.9 parts of sodium carbonate and 146 parts of 1-butanol was refluxed overnight. After cooling, the reaction mixture was filtered and the filtrate was evaporated. The residual oil was partitioned between water and dichloromethane. The organic layer was dried, filtered and evaporated. The residue was crystallized from ethyl acetate, yielding 5.64 parts (42.6%) of trans-1,2,3,4-tetrahydro-2,3-dimethyl-9-nitro-5H-1,4-benzodiazepin-5-one; mp. 169.5° C. (interm. 4).

c) To a mixture of 7.76 parts of intermediate 4 and 445 parts of tetrahydrofuran there were added 104 parts of a solution of borane tetrahydrofuran complex in tetrahydrofuran 1M. After refluxing for 4 days, there were added 50 parts of water and 150 ml of NaOH (3N). Refluxing was continued for 3 hours. The organic layer was separated, washed with NaCl (sat.) (2×), dried, filtered and evaporated. The residue was purified by flash column chromatography (silica gel; $CH_2Cl_2/CH_3OH/NH_4OH$ 93:7:0.1). The eluent of the desired fraction was evaporated, yielding 0.4 parts (5.5%) of (2,3-trans)-2,3,4,5-tetrahydro-2,3-dimethyl-9-nitro-1H-1,4-benzodiazepine (interm. 5).

d) A mixture of 0.34 parts of intermediate 5; 0.23 parts of 1-bromo-3-methyl-2-butene, 0.33 parts of sodium carbonate, 0.26 parts of potassium iodide and 9.4 parts of N,N-dimethylformamide was stirred overnight at room temperature. The reaction mixture was partitioned between ethyl acetate and water. The organic layer was washed with water and NaCl (sat.), dried, filtered and evaporated. The residue was purified by flash column chromatography (silica gel; $CH_2Cl_2/CH_3OH/NH_4OH$ 93:7:0.1). The eluent of the desired fraction was evaporated and the residual oil crystallized on standing, yielding 0.18 parts (40.4%) of (2,3-trans)-2,3,4,5-tetrahydro-2,3-dimethyl-4-(3-methyl-2-butenyl)-9-nitro-1H-1,4-benzodiazepine (interm. 6).

e) To a cooled (0° C.) mixture of 0.18 parts of intermediate 6 and 8.9 parts of tetrahydrofuran there were added 0.095 parts of lithium aluminum hydride. The whole was allowed to warm to room temperature and was then refluxed for 45 min. To the reaction mixture there were added successively 100 parts of water, 300 ml of NaOH (3N) and 100 parts of water. After stirring for ½ hour, the mixture was filtered, dried, filtered and evaporated, yielding 0.17 parts (100%) of (2,3-trans)-2,3,4,5-tetrahydro-2,3-dimethyl-4-(3-methyl-2-butenyl)-1H-1,4-benzodiazepin-9-amine (interm. 7).

EXAMPLE 3 a) To a slightly heated mixture of 37.3 parts of intermediate 3 and 142 parts of 1,1'-oxybisethane there was added a solution of 35.0 parts of (diethyl propanedioato-O", O''') ethoxy magnesium in 92.3 parts of 1,1'-oxybisethane under an Argon atmosphere. Heating was continued for 1½ hours. Then there was added a solution of 19 parts of sulfuric acid in 150 parts of water. The organic layer was separated, washed with NaCl (sat.), dried, filtered and evaporated. The residue was refluxed for 6 hours in a mixture of 28 parts of water, 4.41 parts of acetic acid and 9.75 parts of sulfuric acid. After cooling, the whole was basified with NaOH (3N) and extracted with 1,1'-oxybisethane. The extract was dried, filtered and evaporated, yielding 29.9 parts (86.9%) of 1-(2-bromo-3-nitro-phenyl)ethanone (interm. 8).

b) To 29.6 parts of intermediate 8 there were added 12.9 parts of sodium carbonate and 486 parts of 1-butanol under an Argon atmosphere. The whole was heated till complete solution and then there were added 9.0 parts of 1,2-propanediamine. After refluxing for 4 hours, the reaction mixture was evaporated. The residue was partitioned between dichloromethane and water. The organic layer was separated, dried, filtered and evaporated. The residue was purified by column chromatography (HPLC; silica gel; $CH_3COCH_3$/hexane 20:80). The eluent of the desired fraction was evaporated, yielding 11.4 parts (43.0%) of 2,3-dihydro-3,5-dimethyl-9-nitro-1H-1,4-benzodiazepine (interm. 9).

c) A mixture of 11.35 parts of intermediate 9; 79 parts of methanol and 3.9 parts of sodium cyanotrihydroborate was stirred overnight at room temperature under an Argon atmosphere. There were added an additional 0.2 parts of sodium cyantrihydroborate and some methanol saturated with hydrochloric acid. The reaction mixture was acidified to pH 1 with hydrochloric acid (3N). The solvent was evaporated and the base was set free. The residue was purified by column chromatography (HPLC; silica gel; $CH_3COCH_3$/hexane 1:1). The eluent of the desired fraction was evaporated, yielding 2.3 parts (20.1%) of cis-2,3,4,5-tetrahydro-3,5-dimethyl-9-nitro-1H-1,4-benzodiazepine; mp. 62.0° C. (interm. 10).

d) To 2.18 parts of intermediate 10 there were added successively 1.6 parts of sodium carbonate, 1.64 parts of potassium iodide, 23.5 parts of N,N-dimethylformamide and a solution of 1.81 parts of 1-bromo-3-methyl-2-butene in 23.5 parts of N,N-dimethylformamide. After stirring overnight at room temperature, the reaction mixture was evaporated. The residue was partitioned between dichloromethane and $K_2CO_3$ (aq.). The organic layer was separated, dried, filtered and evaporated. The residue was converted into the (E)-2-butenedioate (2:1) salt in 2-propanol. The product was filtered off and dried, yielding 2.82 parts (82.4%) of cis-2,3,4,5-tetrahydro-3,5-dimethyl-4-(3-methyl-2-butenyl)-9-nitro-1H-1,4-benzodiazepine (E)-2-butenedioate (2:1); mp. 128.0° C. (interm. 11).

e) To a cooled (ice-bath) mixture of 1.73 parts of lithium aluminum hydride and 44.5 parts of tetrahydrofuran there was added slowly a solution of 3.28 parts of intermediate 11 in 35.6 parts of tetrahydrofuran under an Argon atmosphere. The whole was stirred at 0° C. for ½ hour, at room temperature for 3 hours and at reflux temperature for 7 hours. After cooling, there were added slowly 1.7 parts of water, 1.7 ml of NaOH (3N), 5.1 parts of water and 89 parts of tetrahydrofuran. The mixture was filtered and the precipitate was washed with 178 parts of hot tetrahydrofuran. The combined filtrates were evaporated, yielding 2.82 parts (96.2%) of cis-2,3,4,5-tetrahydro-3,5-dimethyl-4-(3-methyl-2-butenyl)-1H-1,4-benzodiazepin-9-amine (interm. 12).

In a similar manner there were also prepared:
2,3,4,5-tetrahydro-5-methyl-4-(3-methyl-2-butenyl)-1H-1,4-benzodiazepin-9-amine (interm. 13);
2,3,4,5-tetrahydro-5-methyl-4-propyl-1H-1,4-benzodiazepin-9-amine (interm. 14); trans-2,3,4,5-tetrahydro-3,5-dimethyl-4-(3-methyl-2-butenyl)-1H-1,4-benzodiazepin-9-amine (interm. 15);

(2,5-trans)-2,3,4,5-tetrahydro-2,5-dimethyl-4-(3-methyl-2-butenyl)-1H-1,4-benzodiazepin-9-amine (interm. 16);
(2,5-cis)-2,3,4,5-tetrahydro-2,5-dimethyl-4-(3-methyl-2-butenyl)-1H-1,4-benzodiazepin-9-amine (interm. 17); and
[3S-(3α,5β)]-7-chloro-2,3,4,5-tetrahydro-3,5-dimethyl-4-(3-methyl-2-butenyl)-1H-1,4-benzodiazepin-9-amine (interm. 18).

EXAMPLE 4

To a solution of 1.34 parts of 7-chloro-2,3,4,5-tetrahydro-5-methyl-4-(3-methyl-2-butenyl)-9-nitro-1H-1,4-benzodiazepine (prepared as intermediate 11) in methanol there were added 0.49 parts of Raney nickel. To the resulting suspension there was added dropwise a solution of 1.09 parts of hydrazine in a small amount of methanol, at reflux temperature and under an Argon atmosphere. Refluxing was continued for 1½ hour. After cooling, the catalyst was filtered off and the filtrate was evaporated, yielding 1.3 parts (100%) of 7-chloro-2,3,4,5-tetrahydro-5-methyl-4-(3-methyl-2-butenyl)-1H-1,4-benzodiazepin-9-amine (interm. 19).

EXAMPLE 5 a) A mixture of 2.6 parts of methyl 2-bromo-3-nitrobenzoate, 1.75 parts of 2-[(phenylmethyl)amino]-propanamine, 1.06 parts of sodium carbonate and 8 parts of 1-butanol was stirred for ½ hour at reflux temperature. The reaction mixture was evaporated and the residue was diluted with 20 parts of water. The product was extracted with trichloromethane (2×30 parts) and the combined extracts were dried, filtered and evaporated. The residue was converted into the monohydrochloride salt in 2-propanol. The product was filtered off, washed with 2-propanol and dried, yielding 3.4 parts (89.5%) of methyl 2-[2-[(phenylmethyl)amino]-propylamino]-3-nitrobenzoate monohydrochloride; mp. 204° C. (interm. 20).

b) A mixture of 3.8 parts of intermediate 20; 15 parts of NaOH (2N) and 4 parts of 2-propanol was stirred for 1 hour at reflux temperature. While refluxing, there was added a solution of 3 parts of concentrated hydrochloric acid and 5 parts of water. After cooling, the precipitated product was filtered off, washed with water and recrystallized from acetic acid, yielding 3 parts (82%) of 2-[[2-methyl-2-[(phenylmethyl)amino]ethyl]amino]-3-nitrobenzoic acid; mp. 227° C. (interm. 21).

c) A mixture of 189.3 parts of intermediate 21; 400 parts of thionyl chloride and 400 parts of methylbenzene was stirred for 2 hours at reflux temperature. The reaction mixture was evaporated and the residue was taken up in 600 parts of methylbenzene. The whole was neutralized with NaHCO$_3$ (aq.). The organic layer was separated, dried, filtered and concentrated. The residue was left at room temperature. The precipitate was filtered off, washed with 2-propanol and 1,1'-oxybisethane and dried, yielding 123.5 parts of product. The mother liquor was evaporated and the residue was recrystallized from boiling 2-propanol. The product was filtered off at room temperature, washed with 2-propanol and 1,1'-oxybisethane and dried, yielding an additional 28 parts of product. The combined crops were recrystallized from ethanol, yielding 137 parts (85%) of 2,3,4,5-tetrahydro-3-methyl-9-nitro-4-(phenylmethyl)-1H-1,4-benzodiazepin-5-one; mp. 125° C. (interm. 22).

d) To a stirred and refluxing suspension of 14 parts of lithium aluminum hydride in 40 parts of benzene and 50 parts of tetrahydrofuran there was added a solution of 20.2 parts of intermediate 22 in 200 parts of tetrahydrofuran. Stirring at reflux temperature was continued for 2.5 hours. After cooling on ice, there were added successively water, NaOH 15% and water. The whole was filtered and the filtrate was evaporated. The residue was co-evaporated with 40 parts of methylbenzene, yielding 19.8 parts (87.6%) of 9-amino-2,3,4,5-tetrahydro-3-methyl-4-(phenylmethyl)-1H-1,4-benzodiazepine (which was used without further purification in the next reaction step) (interm. 23).

EXAMPLE 6 a) To a stirred and cooled (−12° C.) mixture of 9.10 parts of 2-amino-3-nitrobenzoic acid, 6.95 parts of methyl L-α-alanine monohydrochloride, 13.50 parts of 1-hydroxy-1H-1,2,4-benzotriazole monohydrate and 178 parts of tetrahydrofuran there were added portionwise 5.05 parts of N-methylmorpholine and, after 5 min, 10.3 parts of N,N'-methanetetraylbis[cyclohexanamine] under an argon atmosphere. Stirring was continued for 5½ hours at −12° C. and for 15 hours at room temperature. After cooling to 0° C. for ½ hour, the reaction mixture was filtered and the filtrate was evaporated. The residue was partitioned between ethyl acetate and a saturated sodium hydrogen carbonate solution. The organic layer was separated, washed with NaHCO$_3$ (sat.), dried, filtered and evaporated. The residue was triturated with hexane. The product was filtered off and dried, yielding 13.08 parts (97.9%) of (−)-methyl (S)-2-[(2-amino-3-nitrobenzoyl)amino]propanoate; mp. 132.9° C. (interm. 24).

b) A mixture of 12.58 parts of intermediate 24; 3.50 parts of palladium-on-charcoal catalyst 10% and 158 parts of ethanol was hydrogenated in a Parr apparatus for 4 hours at room temperature and a pressure of 3.1 10$^5$ Pa. The catalyst was filtered off over diatomaceous earth and the filtrate was evaporated. The residue was placed under reduced pressure (3.3 10$^3$ Pa.) and stirred at 150° C. for 10 min and at 202° C. for 40 min. After cooling, the solid was triturated with ethanol. The product was filtered off, washed with ethanol and 1,1'-oxybisethane and dried, yielding 5.58 parts (57.7%) of (+)-(S)-9-amino-3,4-dihydro-3-methyl-1H-1,4-benzodiazepine-2,5-dione (interm. 25).

c) To a suspension of 5.55 parts of lithium aluminum hydride in 154.5 parts of 1,4-dioxane there were added 5.00 parts of intermediate 25 under an argon atmosphere. After refluxing for 5 hours and subsequent cooling to 10° C., there were added successively 5.55 parts of water, 9.16 parts of NaOH (15%) and 16.65 parts of water.

The whole was stirred for 2 hours and then filtered. The precipitate was washed with 178 parts of hot tetrahydrofuran and 133 parts of hot dichloromethane. The combined filtrates were dried, filtered and evaporated. The residue was poured into a solution of 7.36 parts of N-methylmorpholine in 133 parts of dichloromethane. The whole was added dropwise to a solution of 4.82 parts of trichloromethyl chloroformate in 160 parts of dichloro-methane at 0° C. under an argon stream. Stirring at 0° C. was continued for 10 min. After warming to room temperature, the reaction mixture was evaporated and there was added 70 parts of an aqueous 1,4-dioxane solution (15%) to the residue. The mixture was heated on a steam-bath for 45 min under a nitrogen stream, cooled and extracted with dichloromethane (2×66.5 parts). The aqueous layer was filtered and basified with concentrated ammonium hydroxide. The precipitate was filtered off, washed with cold water, dried and triturated with 2-propanol (2×), yielding 1.59 parts (32.1%) of (+)-(S)-4,5,6,7-tetrahydro-5-methylimidazo[4,5,1-jk][1,4]benzodiazepin-2(1H)-one; mp. 206.5° C. (interm. 26). In a similar manner there were also prepared:

(−)-(R)-4,5,6,7-tetrahydro-5-methylimidazo[4,5,1-jk][1,4]benzodiazepin-2(1H)-one; mp. 207.8° C. (interm. 27);

4,5,6,7-tetrahydro-5,8-dimethylimidazo[4,5,1-jk][1,4]benzodiazepin-2(1H)-one; mp. 244.8° C. (interm. 28); and (+)-(S)-4,5,6,7-tetrahydro-5,8-dimethylimidazol[4,5,1-jk][1,4]benzodiazepin-2(1H)-one; mp. 207.8° C. (interm. 29).

d) To a cooled (−35° C.) mixture of 7.4 parts of intermediate 26 and 395 parts of acetonitrile there were added 24.8 parts of (1,1-dimethylethoxy)formic acid anhydride and 0.45 parts of N,N-dimethyl-4-pyridinamine. The whole was left for 12 hours at room temperature and was then evaporated. The residue was purified by flash column chromatography (silica gel; $CH_2Cl_2/CH_3OH$ 99:1). The eluent of the desired fraction was evaporated and the residue was stirred for 3 hours in a mixture of 79 parts of methanol and 1.5 parts of potassium carbonate. The solvent was evaporated and the residue was partitioned between ethyl acetate and water. The organic layer was separated, dried, filtered and evaporated, yielding 6.4 parts (57.5%) of (1,1-dimethylethyl) (S)-1,2,4,5,6,7-hexahydro-5-methyl-2-oxoimidazo[4,5,1-jk][1,4]benzodiazepine-6-carboxylate (interm. 30).

e) 5.43 parts of intermediate 30 and 224 parts of trichloromethane were combined at room temperature under argon. After cooling to −35° C., there were added 2.29 parts of N-bromosuccinimide. The whole was kept at −35° C. for 6 hours, allowed to warm to room temperature and left for 12 hours. The reaction mixture was evaporated and the residue was purified by column chromatography (LC; RP). The eluent of the desired fraction was evaporated, yielding 0.5 parts (7.3%) of (1,1-dimethylethyl) (+)-(S)-10-bromo-1,2,4,5,6,7-hexahydro-5-methyl-2-oxoimidazo[4,5,1-jk][1,4]benzodiazepine-6-carboxylate; mp. 228.7° C.; $[\alpha]_D^{25} = +75.8°$ (conc.=0.55 in methanol) (interm. 31).

f) 5.43 parts of intermediate 30 and 224 parts of trichloromethane were combined at room temperature under argon. After cooling to −35° C., there were added 2.29 parts of N-bromosuccinimide. The whole was kept at −35° C. for 6 hours, allowed to warm to room temperature and left for 12 hours. The reaction mixture was evaporated and the residue was purified by column chromatography (LC; RP). The eluent of the desired fraction was evaporated, yielding 2.10 parts (30.7%) of (1,1-dimethylethyl) (−)-(S)-8-bromo-1,2,4,5,6,7-hexahydro-5-methyl-2-oxoimidazo[4,5,1-jk][1,4]benzodiazepine-6-carboxylate; mp. 228.6° C.; $[\alpha]_D^{25} = -60.0°$ (conc.=0.30 in methanol) (interm. 32).

EXAMPLE 7 a) To a cooled (−5° C.) mixture of 20.0 parts of 2-amino-3-nitro-5-(trifluoromethyl)benzoic acid, 11.17 parts of methyl (S)-alanine monohydrochloride, 21.62 parts of 1-hydroxy-1H-1,2,4-benzotriazole monohydrate and 356 parts of tetrahydrofuran under argon there were added 8.1 parts of N-methylmorpholine and, after stirring for 10 min 16.5 parts of N,N-methanetetraylbis[cyclohexanamine]. Stirring was continued for 1 hour at −5° C. and overnight at room temperature. After cooling on ice, the reaction mixture was filtered and the filtrate was evaporated. The residue was dissolved in dichloromethane and this solution was washed with $NaHCO_3$ (aq.), dried, filtered and evaporated. The residue was recrystallized from methylcyclohexane (2×), yielding 19.1 parts (71.2%) of methyl (S)-N-[2-amino-3-nitro-5-(trifluoromethyl)benzoyl]alanine; mp. 136.4° C. (interm. 33).

b) A mixture of 26.1 parts of intermediate 33 and 395 parts of ethanol was hydrogenated at $3.4\ 10^5$ Pa and at room temperature with 9.1 parts of palladium-on-charcoal catalyst 10%. After 2 hours, the catalyst was filtered off and the filtrate was evaporated. The residue was purified by column chromatography (silica gel; $CH_2Cl_2$). The eluent of the desired fraction was evaporated and the residue was crystallized from a mixture of methylbenzene and methylcyclohexane (2:1). The product was filtered off and dried, yielding 5.66 parts (23.8%) of methyl (S)-N-[2,3-diamino-5-(trifluoromethyl)benzoyl]alanine; mp. 96.0° C. (interm. 34).

c) A mixture of 20.56 parts of intermediate 34; 19.6 parts of pyridine and 20 parts of pyridine monohydrochloride was refluxed for 23 hours under argon. The reaction mixture was partitioned between dichloromethane and $NaHCO_3$ (aq.). After filtration, the organic layer was separated, dried, filtered and evaporated. To the residue there were added 399 parts of dichloromethane. The precipitate was filtered off, yielding 6.35 parts (34.5%) of product. The filtrate was evaporated and the residue was purified by flash column chromatography (silica gel; $CH_2Cl_2/CH_3OH$ 19:1). The eluent of the desired fractions was evaporated and the residue was crystallized from acetonitrile, yielding an additional 0.32 parts (1.74%) of product. Total yield: 6.67 parts (36.2%) of (S)-9-amino-3,4-dihydro-3-methyl-7-(trifluoromethyl)-1H-1,4-benzodiazepine-2,5-dione; mp. 275.3° C. (interm. 35).

d) To a cooled (0° C.) mixture of 3.39 parts of sodium tetrahydroborate and 38.3 parts of 1,2-dimethoxyethane under argon, there were added dropwise 8.32 parts of titanium-(IV)chloride and a solution of 3.0 parts of intermediate 35 in 13.9 parts of 1,2-dimethoxyethane. The whole was stirred for 6 days at room temperature and was then partitioned between $NH_4OH$ (conc.) and dichloromethane. The mixture was filtered and the organic layer was separated. The precipitate was washed with dichloromethane and the combined dichloromethane layers were evaporated. The residue was stirred in 40 ml of HCl (3N) for 1 hour. After basifying with NaOH (3N), the product was extracted with dichloromethane. The extract was dried, filtered and evaporated. The residue was purified by column chromatography (silica gel; $CH_2Cl_2/CH_3OH$ 9:1). The eluent of the desired fraction was evaporated, yielding 1.14 parts (42.3%) of (S)-2,3,4,5-tetrahydro-3-methyl-7-(trifluoromethyl)-1H-1,4-benzodiazepin-9-amine (interm. 36).

e) To a cooled (0° C.) solution of 1.06 parts of intermediate 36; 1.32 parts of N-methylmorpholine and 53.2 parts of dichloromethane under argon, there was added dropwise a solution of 0.86 parts of trichloromethyl chloroformate in 26.6 parts of dichloromethane. After stirring for 12 min at 0° C., the reaction mixture was washed with $NaHCO_3$ (sat.), dried, filtered and evaporated. The residue was purified twice by flash column chromatography (silica gel; $CH_2Cl_2/CH_3OH$ 98:2; $CH_2Cl_2/CH_3OH$ 99.5:0.5), The eluent of the desired fraction was evaporated and the residue was heated on a steam bath for 1½ hours in a mixture of water and 1,4-dioxane (85:15). The whole was evaporated and the residue was dissolved in dichloromethane. This solution was washed with $NaHCO_3$, dried, filtered and evaporated, yielding 0.75 parts (63.9%) of (S)-4,5,6,7-tetrahydro-5-methyl-9-(trifluoromethyl)imidazo[4,5,1-jk][1,4]-benzodiazepin-2(1H)-one (interm. 37).

EXAMPLE 8 a) To a stirred solution of 11.8 parts of 1-propanamine in 24.9 parts of 1,1'-oxybis ethane there was added dropwise a solution of 18.1 parts of ethyl 2-bromopropanoate in 24.9 parts of 1,1'-oxybisethane. After stirring for 72 hours at room temperature, the reaction mixture was filtered and the filtrate was rinsed with 1,1'-oxybisethane. The combined 1,1'-oxybisethane layers were evaporated, yielding 15.9 parts (100%) of ethyl N-propylalanine as a residue (interm. 38).

b) A mixture of 9.90 parts of 2-amino-3-nitrobenzoic acid and 32.4 parts of thionyl chloride was stirred for 15 min at reflux temperature under argon. The excess of thionyl chloride was evaporated, yielding 10.8 parts (100%) of 2-amino-3-nitrobenzoyl chloride (interm. 39).

c) To a stirred and cooled (0° C.) solution of 8.65 parts of intermediate 38 and 5.52 parts of N,N-diethylethanamine in 53.2 parts of dichloromethane there was added dropwise a suspension of 10.83 parts of intermediate 39 in 119.7 parts of dichloromethane under argon. Stirring was continued for 5 min at 0° C. and for 1 hour at room temperature. The reaction mixture was washed successively with water, $NaHCO_3$ (sat.), citric acid (2N) and again $NaHCO_3$ (sat.) and was then dried, filtered and evaporated, yielding 19.14 parts (100%) of ethyl N-(2-amino-3-nitrobenzoyl)-N-propylalanine (interm. 40).

d) A solution of 17.5 parts of intermediate 40 in 80 parts of ethanol was hydrogenated at 3.5 $10^5$ Pa and at room temperature with 2.0 parts of palladium-on-charcoal catalyst 10%. After the calculated amount of hydrogen was taken up, the catalyst was filtered off over diatomaceous earth and the filtrate was evaporated. The residual oil was heated in vacuo (3.3 $10^3$ Pa) in an oil bath (100° C.) for 1½ hours. After cooling, the oil was purified by column chromatography (silica gel; $CH_2Cl_2/CH_3OH$ 20:1). The eluent of the desired fraction was evaporated, yielding 4.6 parts (34.4%) of 9-amino-3-methyl-4-propyl-3H-1,4-benzodiazepine-2,5(1H,4H)-dione (interm. 41).

e) To a stirred and cooled (0° C.) suspension of 1.28 parts of lithium aluminum hydride in 52 parts of 1,2-dimethoxyethane under argon, there were added dropwise 1.39 parts of intermediate 41. Stirring was continued for 2 hours at 0° C. and for 72 hours at reflux temperature. After cooling, there were added successively a solution of 1.3 parts of water and 3.6 parts of tetrahydrofuran, 1.3 parts of NaOH (15%) and 3.9 parts of water. The whole was stirred for 1 hour and then filtered. The precipitate was refluxed for 5 min in 45 parts of tetrahydrofuran and filtered off again. The combined filtrates were dried, filtered and evaporated, yielding 1.24 parts (100%) of 2,3,4,5-tetrahydro-3-methyl-4-propyl-1H-1,4-benzodiazepin-9-amine (interm. 42).

EXAMPLE 9 a) A mixture of 17.7 parts of 6-methyl-4H-3,1-benzoxazine-2,4(1H)-dione, 15.0 parts of methyl 2-aminopropanoate monohydrochloride and 62.7 parts of pyridine was refluxed for 6 hours under argon. The reaction mixture was cooled at −10° C. for 1 hour. The precipitate was filtered off, rinsed with water, triturated in ethanol and rinsed with ethanol and 1,1'-oxybisethane, yielding 10.32 parts (50.5%) of 3,4-dihydro-3,7-dimethyl-1H-1,4-benzodiazepine-2,5-dione (interm. 43).

b) To a cooled (0° C.) amount of 61.9 parts of concentrated nitric acid there were added dropwise 9.50 parts of intermediate 43 under argon. The mixture was left at 0° C. for 1 hour and was then slowly added to 160 parts of ice-water while stirring. The precipitate was filtered off, rinsed with water and dried overnight at room temperature, yielding 9.92 parts (85.5%) of 3,4-dihydro-3,7-dimethyl-9-nitro-1H-1,4-benzodiazepine-2,5-dione (interm. 44).

c) To a cooled (0° C.) suspension of 10.35 parts of lithium aluminum hydride in 305 parts of 1,2-dimethoxyethane there were added 9.71 parts of intermediate 44 under argon. After refluxing for 72 hours and subsequent cooling, there were added successively a mixture of 10.35 parts of water and 31 parts of tetrahydrofuran, 10.35 ml of NaOH (15%) and 31.05 parts of water. The whole was stirred for 1 hour and was then filtered. The precipitate was refluxed in tetrahydrofuran for 5 min and filtered off again. The combined filtrates were dried, filtered and evaporated. The residual oil was immediately combined with a mixture of 11.8 parts of N-methylmorpholine and 79.8 parts of dichloromethane and the whole was added to a mixture of 7.7 parts of trichloromethyl chloroformate and 120 parts of dichloromethane at 0° C. under argon. The mixture was stirred for 5 min at 0° C. and evaporated. The residue was heated on a steam-bath for 1 hour in 100 ml of a mixture of water and dioxane (85:15) under argon. The solution was cooled, basified with $NH_4OH$ and extracted with dichloromethane (2×46.6 parts). The combined extracts were dried, filtered and evaporated. The residue was triturated with 2-propanol and recrystallized from 2-propanol. The product was filtered off, rinsed with 2-propanol and 1,1'-oxybisethane, yielding 0.55 parts (6.5%) of 4,5,6,7-tetrahydro-5,9-dimethylimidazo[4,5,1-jk][1,4]benzodiazepin-2(1H)-one; mp. 199.2° C. (interm. 45).

In a similar manner there were also prepared the intermediates listed in Table 1 hereinbelow.

TABLE 1

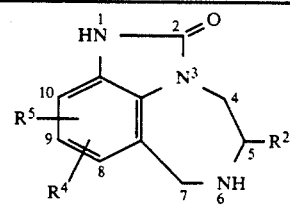

| Int. No. | R² | R⁴ | R⁵ | Physical data |
|---|---|---|---|---|
| 47 | $CH_3$ | 9-Cl | H | (±); mp. 199.0° C. |
| 48 | $CH_3$ | 9-Cl | H | (+)-(S); mp. 202.2° C. $[\alpha]_D^{20}$ 0.98% $CH_3OH$ = +72.6° |
| 49 | $CH_3$ | 9-Cl | H | (−)-(R); mp. 200.8° C. $[\alpha]_D^{20}$ 1.01% $CH_3OH$ = −68.6° |
| 50 | H | 9-Cl | H | mp. 238–244° C. |

TABLE 1-continued

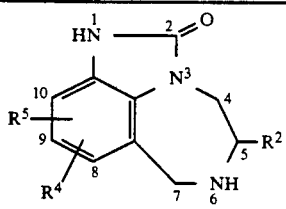

| Int. No. | R² | R⁴ | R⁵ | Physical data |
|---|---|---|---|---|
| 51 | CH₃ | 9-F | H | (S); mp. 222.1° C. |
| 52 | CH₃ | 9-Cl | 10-Cl | (S) |

EXAMPLE 10 a) To a stirred suspension of 6.85 parts of intermediate 39 and 4.7 parts of 1-amino-3-methyl-2-butanone monohydrochloride in 113 parts of dichloromethane there was added dropwise a solution of 6.9 parts of N,N-diethylethanamine in 20 parts of dichloromethane under a nitrogen atmosphere. Stirring was continued for 21 hours. The reaction mixture was washed with water and the washings were re-extracted with dichloromethane. The combined dichloromethane layers were washed with water, NaHCO₃ (sat.) and NaCl (sat.) and were then dried, filtered and evaporated. The residue was recrystallized from ethanol. The hot solution was filtered and the filtrate was evaporated, yielding 6 parts (66.5%) of 2-amino-N-(3-methyl-2-oxobutyl)-3-nitrobenzamide (interm. 53).

b) A mixture of 5.9 parts of intermediate 53; 2.37 parts of palladium-on-charcoal catalyst 10% and 119 parts of ethanol was hydrogenated in a Parr apparatus at 3.6 10⁵ Pa for 50 hours. The catalyst was filtered off over diatomaceous earth, which was rinsed with ethanol and dichloromethane. The combined filtrates were evaporated, yielding 4.64 parts (96.0%) of 9-amino-3,4-dihydro-2-(1-methylethyl)-5H-1,4-benzodiazepin-5-one (interm. 54).

c) To a stirred suspension of 4.75 parts of intermediate 54 in 155 parts of 1,4-dioxane there were added 5.0 parts of lithium aluminum hydride under argon. The whole was heated at 90°-110° C. for 6 days and subsequently cooled on ice. There were added successively a mixture of 5 parts of water and 22.3 parts of tetrahydrofuran, 5 ml of NaOH (3N) and 15 parts of water. After stirring for 2 hours at 0° C., the mixture was dried and filtered. The solid was washed with 266 parts of hot dichloromethane and the combined filtrates were evaporated, yielding 4.7 parts (100%) of 2,3,4,5-tetrahydro-2-(1-methylethyl)-1H-1,4-benzodiazepin-9-amine (interm. 55).

d) To a stirred and cooled (0° C.) solution of 4.51 parts of trichloromethyl chloroformate in 133 parts of dichloromethane under argon, there was added dropwise a solution of 4.7 parts of intermediate 55 and 7.0 parts of N-methylmorpoline in 66.5 parts of dichloromethane. Stirring was continued for 2½ hour at 0° C. The reaction mixture was evaporated and the residue was heated on a steam-bath for 5 hours in a mixture of 15 parts of water and 87.6 parts of 1,4-dioxane. After cooling, the mixture was washed with dichloromethane (3×) and then basified with NH₄OH. The product was extracted with dichloromethane (3×) and the extract was washed with water and NaCl (sat.), dried, filtered and evaporated. The residue was purified by flash column chromatography (silica gel; CH₂Cl₂/C₂H₅OH 96:4). The eluent of the desired fraction was evaporated and the residue was triturated with acetonitrile. The product was filtered off and dried in an Abderhalen (2-propanol reflux) overnight, yielding 0.67 parts (12.6%) of 4,5,6,7-tetrahydro-4-(1-methylethyl)imidazo[4,5,1-jk][1,4]benzodiazepin-2(1H)-one; mp. 167.4° C. (interm. 56). In a similar manner there were also prepared:

4,5,6,7-tetrahydro-4-propylimidazo[4,5,1-jk][1,4]benzodiazepin-2(1H)-one; mp. 160.7° C. (interm. 57); and 4,5,6,7-tetrahydro-4-methylimidazo[4,5,1-jk][1,4]benzodiazepin-2(1H)-one; mp. 220.2° C. (interm. 58).

EXAMPLE 11 a) To a cooled (0° C.) suspension of 8.53 parts of lithium aluminum hydride in 392 parts of 1,2-dimethoxyethane there were added dropwise 20.19 parts of (S)-7-chloro-3,4-dihydro-3-methyl-1H-1,4-benzodiazepine-2,5-dione (prepared as intermediate 43) under argon. The mixture was left at room temperature for 3 hours and was then refluxed for 29 hours. After cooling to 0° C., there were added successively a mixture of 8.5 parts of water and 22.7 parts of tetrahydrofuran, 9.86 parts of NaOH (15%) and 25.5 parts of water. The whole was stirred for 24 hours and was then filtered. The precipitate was refluxed in 178 parts of tetrahydrofuran for 5 min and filtered off again. The combined filtrates were evaporated and the residual oil crystallized on standing, yielding 18.4 parts (100%) of (S)-7-chloro-2,3,4,5-tetrahydro-3-methyl-1H-1,4-benzodiazepine (interm. 59).

b) To a cooled (0° C.) solution of 3.92 parts of intermediate 59 and 2.03 parts of N,N-diethylethanamine in 53.2 parts of dichloromethane there was added dropwise a solution of 2.1 parts of cyclopropylcarbonyl chloride in 26.6 parts of dichloromethane under argon. The mixture was left at room temperature for 24 hours and was then filtered. The filtrate was washed with NaHCO₃ (sat.), dried, filtered and evaporated, yielding 2.88 parts (54.4%) of (S)-7-chloro-4-(cyclopropylcarbonyl)-2,3,4,5-tetrahydro-3-methyl-1H-1,4-benzodiazepine (interm. 60).

c) To a cooled (0° C.) amount of 7.6 parts of conc. nitric acid there were added portionwise 1.59 parts of intermediate 60 under argon. After cooling at 0° C. for ½ hour, the reaction mixture was slowly added to 50 parts of ice-water while stirring. The precipitate was filtered off, rinsed with 50 parts of ice-water and dried, yielding 1.91 parts (98.5%) of (S)-7-chloro-4-(cyclopropylcarbonyl)-2,3,4,5-tetrahydro-3-methyl-9-nitro-1H-1,4-benzodiazepine (interm. 61).

d) To a cooled (0° C.) suspension of 1.37 parts of lithium aluminum hydride in 30.5 parts of 1,2-dimethoxyethane there were added portionwise 1.79 parts of intermediate 61 under argon. The mixture was left at room temperature for ½ hour and was then refluxed for 15 hours. After cooling to 0° C., there were added successively a mixture of 1.4 parts of water and 3.7 parts of tetrahydrofuran, 1.6 parts of NaOH 15% and 4.2 parts of water. The whole was stirred for 1 hour and then filtered. The precipitate was refluxed in 31 parts of tetrahydrofuran for 5 min and filtered off again. The combined filtrates were evaporated and the residual oil was used without further purification, yielding (S)-7-chloro-4-(cyclopropylmethyl)-2,3,4,5-tetrahydro-3-methyl-1H-1,4-benzodiazepin-9-amine (interm. 62).

EXAMPLE 12 a) To a cooled (0° C.) mixture of 18.9 parts of (S)-N-[(1,1-dimethylethoxy)carbonyl]alanine, 10.8 parts of 2-methyl-2-propen-1-amine monohydrochloride, 27.0 parts of 1-hydroxy-1H-benzotriazole hydrate and tetrahydrofuran, there were added 10.1 parts of N-methylmorpholine and, after 20 min, 20.6 parts of N,N-methanetetraylbis[cyclohexanamine] under a nitrogen atmosphere. The whole was kept at 0° C. for 1 hour and at room temperature for 12 hours. The solvent was evaporated and the residue was partitioned between dichloromethane and NaHCO$_3$ (sat.). The organic layer was separated, washed with NaCl (sat.), dried, filtered and evaporated, yielding 24.2 parts (99.9%) of (1,1-dimethylethyl) (S)-[1-methyl-2-[(2-methyl-2-propenyl)amino]-2-oxoethyl]carbamate (interm. 63).

b) To a cooled (0° C.) amount of 88.8 parts of trifluoroacetic acid there were slowly added 14.3 parts of intermediate 63. The mixture was kept at 0° C. for 3 hours and was then evaporated. The residual oil was extracted with NaHCO$_3$ (sat.) and the aqueous layer was continuously extracted with dichloromethane overnight. The extract was dried, filtered and evaporated, yielding 4.2 parts (49.2%) of (S)-2-amino-N-(2-methyl-2-propenyl)propanamide (interm. 64).

c) To a solution of 3.2 parts of lithium aluminum hydride in 22.3 parts of tetrahydrofuran there was slowly added a solution of 4.2 parts of intermediate 64 in 22.3 parts of tetrahydrofuran under argon. After refluxing for 16 hours and subsequent cooling to 0° C., there were added successively 3.2 parts of water, 9.6 ml of NaOH (3N) and 3.2 parts of water. The whole was filtered and the solid was washed with 22.3 parts of tetrahydrofuran. The combined filtrates were dried, filtered and evaporated, yielding 2.0 parts (46.8%) of (S)-N$^1$-(2-methyl-2-propenyl)-1,2-propanediamine (interm. 65).

d) A mixture of 5.0 parts of 2,5-dichloro-3-nitrobenzoic acid and 16.2 parts of thionyl chloride was refluxed for 24 hours under argon. The reaction mixture was evaporated, yielding 4.74 parts (87.5%) of 2,5-dichloro-3-nitrobenzoyl chloride (interm. 66).

e) A mixture of 4.0 parts of intermediate 66; 40.5 parts of 1-butanol and 5.4 parts of sodium carbonate was refluxed for 2 hours under argon. There were added 2.0 parts of intermediate 65 and refluxing was continued for 16 hours. The reaction mixture was filtered and the filtrate was evaporated. The residue was purified by flash column chromatography (silica gel; CH$_2$Cl$_2$/CH$_3$OH 99:1). The eluent of the desired fraction was evaporated, yielding 1.43 parts (27.2%) of (+)-(S)-7-chloro-1,2,3,4-tetrahydro-2-methyl-4-(2-methyl-2-propenyl)-9-nitro-5H-1,4-benzodiazepin-5-one; mp. 66.5° C.; [α]$_D^{25}$=+314.5° (conc.=0.325% in CH$_3$OH) (interm. 67).

In a similar manner there was also prepared:
(−)-(R)-7-chloro-4-(cyclopropylmethyl)-1,2,3,4-tetrahydro-2-methyl-9-nitro-5H-1,4-benzodiazepin-5-one; mp. 79.7° C.; [α]$_D^{25}$=−314.5° (conc.=0.73% in CH$_3$OH) (interm. 68).

EXAMPLE 13 a) To a homogeneous solution of 8.42 parts of (S)-2-aminopropanamide monohydrobromide, 12.26 parts of sodium acetate and 79 parts of methanol there were added 10.96 parts of 2,6-dichloro-3-nitrobenzaldehyde and, after ½ hour, a mixture of 3.77 parts of sodium cyanotrihydroborate and 7.9 parts of methanol. The whole was stirred for 45 min at room temperature. After acidifying to pH 1 with HCl (3N), stirring was continued overnight. The reaction mixture was evaporated and the residue was basified with NaHCO$_3$ (sat.). The product was extracted with dichloromethane and the extract was dried, filtered and evaporated. The residue was recrystallized from 2-propanol, yielding 10.29 parts (70.7%) of (S)-2-[[(2,6-dichloro-3-nitrophenyl)methyl]amino]propanamide (interm. 69).

b) A mixture of 10.03 parts of intermediate 69; 348 parts of 1,2-dimethoxyethane and 92.5 parts of a solution of borane tetrahydrofurancomplex in tetrahydrofuran 1M was stirred for 3 days at room temperature under argon. There were slowly added 142 parts of methanol and 180 ml of HCl (3N) and stirring was continued over weekend. The reaction mixture was basified with 200 ml of NaOH (3N) and was then evaporated. The residue was extracted with dichloromethane and the extract was dried, filtered and evaporated. The residue was refluxed in a mixture of 3.0 parts of sodium acetate and 81 parts of 1-butanol for 3 days under argon. The solvent was evaporated and the residue was dissolved in dichloromethane. This solution was washed with NaHCO$_3$, dried, filtered and evaporated. The residue was purified twice by flash column chromatography (silica gel; CH$_2$Cl$_2$/CH$_3$OH 99:1). The eluent of the desired fraction was evaporated and the residue was converted into the (E)-2-butenedioate salt in methanol. The salt was filtered off (1st fraction) and the mother liquor was evaporated. The residue was chromatographed and also converted into the salt (2nd fraction). The combined fractions were treated with a mixture of dichloromethane and NaOH (3N) to set free the base, yielding 3.73 (45.0%) of (S)-6-chloro-2,3,4,5-tetrahydro-3-methyl-9-nitro-1H-1,4-benzodiazepine (interm. 70).

c) A mixture of 1.80 parts of intermediate 70; 1.21 parts of sodium carbonate, 1.24 parts of potassium iodide, 9.4 parts of N,N-dimethylformamide and a solution of 1.37 parts of 1-bromo-3-methyl-2-butene in 7.5 parts of N,N-dimethylformamide was stirred overnight at room temperature. The reaction mixture was extracted with dichloromethane and the extract was dried, filtered and evaporated. The residue was purified by flash column chromatography (silica gel; CH$_2$Cl$_2$/CH$_3$OH 98:2). The eluent of the desired fraction was evaporated, yielding 1.93 parts (83.6%) of (S)-6-chloro-2,3,4,5-tetrahydro-3-methyl-4-(3-methyl-2-butenyl)-9-nitro-1H-1,4-benzodiazepine (interm. 71).

d) To a cooled (0° C.) mixture of 0.90 parts of lithium aluminum hydride and 22.3 parts of tetrahydrofuran there was added dropwise a solution of 1.84 parts of intermediate 71 and 22.3 parts of tetrahydrofuran under argon. The whole was stirred for 1 hour at 0° C., for 1½ hours at room temperature and for 8 hours at reflux temperature. After cooling to 0° C., there were added successively a mixture of 0.9 parts of water and 44.5 parts of tetrahydrofuran, 0.9 ml of NaOH (3N) and 2.7 parts of water. The mixture was filtered over diatomaceous earth and the precipitate was washed with hot tetrahydrofuran. The combined filtrates were evaporated, yielding 1.75 parts (100%) of (S)-6-chloro-2,3,4,5-tetrahydro-3-methyl-4-(3-methyl-2-butenyl)-1H-1,4-benzodiazepin-9-amine (interm. 72).

In a similar manner there were also prepared:

(S)-6-chloro-4-(3-ethyl-2-pentenyl)-2,3,4,5-tetrahydro-3-methyl-1H-1,4-benzodiazepin-9-amine (interm. 73); and
6-chloro-2,3,4,5-tetrahydro-4-(3-methyl-2-butenyl)-1H-1,4-benzodiazepin-9-amine (interm. 74).

EXAMPLE 14 a) To a cooled (0° C.) suspension of 2.0 parts of lithium aluminum hydride in 51.5 parts of 1,4-dioxane there was added a solution of 2.1 parts of cis-1,2,3,4-tetrahydro-2,3-dimethyl-9-nitro-5H-1,4-benzodiazepin-5-one (prepared as intermediate 4) in 36.1 parts of 1,4-dioxane. The whole was refluxed overnight. After cooling, there were added successively 2 parts of water, 6 ml of NaOH (3N) and 2 parts of water. The mixture was filtered and the filtrate was evaporated, yielding 1.67 parts (97.8%) of (2,3-cis)-2,3,4,5-tetrahydro-2,3-dimethyl-1H-1,4-benzodiazepin-9-amine (interm. 75).

b) To a cooled (0° C.) solution of 1.66 parts of trichloromethyl chloroformate in 39.9 parts of dichloromethane there was added dropwise a solution of 1.60 parts of intermediate 75 and 2.54 parts of N-methylmorpholine in 66.5 parts of dichloromethane. The whole was stirred over weekend at room temperature and was then evaporated. The residue was heated on a steam-bath for 2 hours in 50 ml of a mixture of 1,4-dioxane and water (15:85). After cooling, the mixture was neutralized with NH$_4$OH (conc.) and extracted with dichloromethane. The extract was washed with NaCl (sat.), dried, filtered and evaporated. The residue was purified by flash column chromatography (silica gel; CH$_2$Cl$_2$/CH$_3$OH/NH$_4$OH 93:7:0.1). The eluent of the desired fraction was evaporated, yielding 0.8 parts (43.9%) of (4,5-cis)-4,5,6,7-tetrahydro-4,5-dimethylimidazo[4,5,1-jk][1,4]benzodiazepin-2(1H)-one (interm. 76).

EXAMPLE 15 a) A mixture of 298.42 parts of (S)-7-chloro-3,4-dihydro-3-methyl-9-nitro-1H-1,4-benzodiazepine-2,5-dione (prepared as interm. 44) and 3324 parts of ethanol was hydrogenated at 50° C. and normal pressure with 21.04 parts of platinum-on-charcoal catalyst 5%. At the end of the hydrogenation, the temperature was raised to 70° C. The reaction mixture was filtered while hot and the catalyst was washed with boiling ethanol. The filtrate was stirred overnight in an ice-bath and was then concentrated. The residue was cooled on ice. The precipitate was filtered off, washed with methylbenzene and dried in vacuo at 50° C., yielding 187.7 parts (74.6%) of (S)-9-amino-7-chloro-3,4-dihydro-3-methyl-1H-1,4-benzodiazepine-2,5-dione (interm. 77).

b) To a cooled (ice-bath) suspension of 29.3 parts of lithium aluminum hydride in 392 parts of 1,2-dimethoxyethane there were added portionwise 30.78 parts of intermediate 77 under a nitrogen atmosphere. The whole was refluxed for 22 hours and subsequently cooled to 0°-5° C. There were added successively a mixture of 36.5 parts of 1,2-dimethoxyethane and 42 parts of water, 48.7 parts of NaOH (15%) and 135 parts of water. After stirring for 15 min, the mixture was filtered and the precipitate was washed with 1,2-dimethoxyethane. The combined filtrates were evaporated and the residue was dried, yielding 25.4 parts (93.7%) of (S)-7-chloro-2,3,4,5-tetrahydro-3-methyl-1H-1,4-benzodiazepin-9-amine (interm. 78).

c) To a heated (40° C.) solution of 91 parts of intermediate 78 in 500 ml of 1,2-dimethoxyethane there were added successively 1253 parts of N,N-dimethylformamide, 66.98 parts of sodium carbonate and 71.38 parts of potassium iodide. After cooling to 0°-5° C., there was added dropwise a solution of 271.3 parts of 1-chloro-3-methyl-2-butene in 270 parts of N,N-dimethylformamide under a nitrogen atmosphere. The whole was stirred for 18 hours at 0°-5° C. and was then partitioned between dichloromethane and water. The aqueous layer was separated and re-extracted with dichloromethane. The combined dichloromethane layers were washed with water (7×x), dried, filtered and evaporated. The residue was purified by column chromatography (silica gel; C$_6$H$_5$CH$_3$/i.C$_3$H$_7$OH 98:2). The eluent of the desired fraction was evaporated, yielding 43.64 parts (51.8%) of (S)-7-chloro-2,3,4,5-tetrahydro-3-methyl-4-(3-methyl-2-butenyl)-1H-1,4-benzodiazepin-9-amine (interm. 79).

EXAMPLE 16

A suspension of 1.0 part of compound 19 in 8.25 parts of phosphoryl chloride was heated for 15 hours at 90° C. under a nitrogen atmosphere. The reaction mixture was evaporated and the residue was parititioned between NaHCO$_3$ (sat.) and dichloromethane. The aqueous layer was re-extracted with dichloromethane. The combined organic layers were washed with NaHCO$_3$ (sat.) and NaCl (sat.), dried, filtered and evaporated, yielding 1.05 parts (98.3%) of 2-chloro-4,5,6,7-tetrahydro-5-methyl-6-(3-methyl-2-butenyl)imidazo[4,5,1-jk][1,4]benzodiazepine (interm. 80).

In a similar manner there was also prepared:
(−)-(S)-2,9-dichloro-6-(cyclopentylmethyl)-4,5,6,7-tetrahydro-5-methylimidazo[4,5,1-jk][1,4]benzodiazepine (interm. 81).

EXAMPLE 17

A suspension of 38.16 parts of compound 27 and 15 parts of sodium carbonate in 578 parts of phosphoryl chloride was stirred for 2 days at 60° C. under a nitrogen atmosphere. The excess of phosphoryl chloride was distilled off under vacuum at 30°-50° C. After cooling on ice, the residue was dissolved in 500 parts of water. This solution was carefully basified with 1000 ml of NaHCO$_3$ (sat.). The product was extracted with dichloromethane (3×355 parts) and the combined extracts were washed with NaHCO$_3$ (sat.) and NaCl (sat.), dried, filtered and evaporated, yielding 27 parts (66.5%) of (S)-2-chloro-4,5,6,7-tetrahydro-5-methyl-6-(3-methyl-2-butenyl)imidazo[4,5,1-jk][1,4]benzodiazepine (interm. 82).

In a similar manner there were also prepared the intermediates listed in Table 2 hereinbelow.

TABLE 2

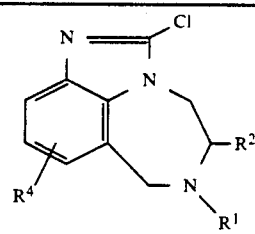

| Rnr | Int. No. | R$^1$ | R$^2$ | R$^4$ | Physical data |
|---|---|---|---|---|---|
| 82.912 | 83 | —CH$_2$—CH=C(CH$_3$)$_2$ | CH$_3$ | 9-Cl | (S) |
| 83.157 | 84 | —CH$_2$—CH=C(CH$_3$)$_2$ | CH$_3$ | H | (R) |
| 84.673 | 85 | —CH$_2$—CH=C(CH$_3$)$_2$ | CH$_3$ | 8-CH$_3$ | (S) |
| 84.965 | 86 | —CH$_2$—CH=C(CH$_3$)$_2$ | CH$_3$ | 9-Cl | (R) |

TABLE 2-continued

[Structure: benzodiazepine with N=C-Cl, N, R², R¹, R⁴ substituents]

| Rnr | Int. No. | R¹ | R² | R⁴ | Physical data |
|---|---|---|---|---|---|
| 85.149 | 87 | —CH₂—CH=C(CH₃)₂ | H | 9-Cl | — |
| 85.172 | 88 | —CH₂—CH=C(CH₃)₂ | CH₃ | 9-F | (S) |
| 85.786 | 89 | —CH₂—[cyclobutyl] | CH₃ | 9-Cl | (S) |
| 86.084 | 90 | —(CH₂)₂—[cyclopropyl] | CH₃ | 9-Cl | (S) |
| 86.161 | 91 | —CH₂—CH=C(C₂H₅)₂ | CH₃ | 9-Cl | (S) |
| 86.177 | 92 | —CH₂—CH=C(CH₃)₂ | CH₃ | 9-CF₃ | (S) |

EXAMPLE 18

To a cooled (−78° C.) solution of 1.23 parts of compound 114 in 93.1 parts of dichloromethane under argon, there were added successively 1.38 parts of trifluoroacetic anhydride, after 10 min, 0.79 parts of 2,6-dimethylpyridine and, after 15 min, 23 ml of a solution of HCl in 1,1'-oxybisethane (0.8N). The whole was left for 15 min and was then poured into NaHCO₃ (sat.). The organic layer was separated, dried, filtered and evaporated, yielding 1.61 parts (100%) of (S)-2,8-dichloro-6-(3-ethyl-2-pentenyl)-4,5,6,7-tetrahydro-5-methylimidazo[4,5,1-jk][1,4]benzodiazepine (interm. 93).

In a similar manner there were also prepared:
(4,5-cis)-2-chloro-4,5,6,7-tetrahydro-4,5-dimethyl-6-(3-methyl-2-butenyl)imidazo[4,5,1-jk][1,4]benzodiazepine (interm. 94); and
(S)-2,9-dichloro-4,5,6,7-tetrahydro-5-methyl-6-(3-methylbutyl)imidazo[4,5,1-jk][1,4]benzodiazepine (interm. 95).

EXAMPLE 19

A mixture of 8 parts of compound 3 in 80 parts of acetic acid was hydrogenated at normal pressure and 38° C. with 1 part of palladium-on-charcoal catalyst 10%. After the calculated amount of hydrogen was taken up, the catalyst was filtered off and the filtrate was evaporated. The residue was taken up in 75 parts of water and the whole was basified with 30 parts of concentrated ammonium hydroxide. The mixture was left to crystallize at room temperature. The product was filtered off and recrystallized from 2-propanol, yielding 3.7 parts (66.8%) of 4,5,6,7-tetrahydro-5-methylimidazo[4,5,1-jk][1,4]benzodiazepin-2(1H)-one; mp. 190.5° C. (interm. 96). In a similar manner there was also prepared:
4,5,6,7-tetrahydroimidazo[4,5,1-jk][1,4]benzodiazepin-2(1H)-one; mp. 208°–220° C. (interm. 97).

EXAMPLE 20 a) To a mixture of 7.76 parts of intermediate 4 and 445 parts of tetrahydrofuran there were added 104 parts of a solution of borane tetrahydrofuran complex in tetrahydrofuran 1M. After refluxing for 4 days, there were added 50 parts of water and 150 ml of NaOH (3N). Refluxing was continued for 3 hours. The organic layer was separated, washed with NaCl (sat.) (2×), dried, filtered and evaporated. The residue was purified by flash column chromatography (silica gel; CH₂Cl₂/CH₃OH/NH₄OH 93:7:0.1). The eluent of the desired fraction was evaporated, yielding 0.51 parts (8.1%) of (2,3-trans)-2,3,4,5-tetrahydro-2,3-dimethyl-1H-1,4-benzodiazepin-9-amine (interm. 98).

b) A mixture of 0.51 parts of intermediate 98; 0.52 parts of 1,1'-thiocarbonylbis[1H-imidazole] and 17.8 parts of tetrahydrofuran was refluxed for 4 hours. The reaction mixture was partitioned between ethyl acetate and water. The organic layer was separated, washed with water (2×) and NaCl (sat.), dried, filtered and evaporated, yielding 0.38 parts (61.0%) of (4,5-trans)-4,5,6,7-tetrahydro-4,5-dimethylimidazo[4,5,1-jk][1,4]benzodiazepine-2(1H)-thione (interm. 99).

B. Preparation of the final compounds

EXAMPLE 21

To a solution of 0.93 parts of intermediate 14; 3.95 parts of ethanol and 1 part of water there were added 0.32 parts of potassium hydroxide and, after 8 min, 0.43 parts of carbon disulfide. The mixture was stirred for 10 min at room temperature and heated for 1 hour at 90° C. After cooling to room temperature, there were added 5.6 parts of water and 0.49 parts of acetic acid. The solid was filtered off and partitioned between diluted ammonium hydroxide and dichloromethane. The organic layer was dried, filtered and evaporated. The residue was triturated in acetonitrile and recrystallized from ethanol, yielding 0.28 parts (25.2%) of 4,5,6,7-tetrahydro-7-methyl-6-propylimidazo[4,5,1-jk][1,4]benzodiazepin-2(1H)-thione; mp. 179.1° C. (comp. 41).

EXAMPLE 22

A mixture of 2.8 parts of intermediate 12; 2.55 parts of 1,1'-carbonothioylbis[1H-imidazole] and 44.5 parts of tetrahydrofuran was refluxed on a steam bath for ½ hour under an argon atmosphere. The reaction mixture was evaporated and the residue was partitioned between dichloromethane and water. The organic layer was separated, dried, filtered and evaporated. The residue was purified by flash column chromatography (silica gel; CH₂Cl₂/CH₃OH 99:1). The eluent of the desired fraction was evaporated and the residue was crystallized from ethanol. The product was filtered off and dried, yielding 1.08 parts (33.2%) of cis-4,5,6,7-tetrahydro-5,7-dimethyl-6-(3-methyl-2-butenyl)imidazo[4,5,1-jk][1,4]benzodiazepine-2(1H)thione; mp. 138.3° C. (comp. 52).

EXAMPLE 23

A mixture of 0.216 parts of intermediate 99; 0.07 parts of cyclopropanecarboxaldehyde, 0.116 parts of sodium cyanotrihydroborate, 55.7 parts of acetic acid, 7.9 parts of methanol and 4.5 parts of tetrahydrofuran was stirred for 2 days at room temperature. The reaction mixture was acidified with HCl and stirring was continued until gas evolution ceased. The whole was neutralized with NaOH (3N) and filtered. The filtrate was evaporated and the residue was partitioned between NaOH (1N) and dichloromethane. The organic layer was dried, filtered and evaporated. The residue was purified by flash column chromatography (silica gel; $CH_2Cl_2/CH_3OH/NH_4OH$ 95:5:0.1). The eluent of the desired fraction was evaporated and the residue was crystallized from 1,1'-oxybisethane. The product was filtered off and dried in vacuo at room temperature overnight, yielding 0.13 parts (49.1%) of (4,5-trans)-6-(cyclopropylmethyl)-4,5,6,7-tetrahydro-4,5-dimethylimidazo[4,5,1-jk][1,4]benzodiazepine-2(1H)-thione; mp. 135.2° C. (comp. 57).

EXAMPLE 24

A solution of 0.71 parts of intermediate 19; 0.45 parts of 1,1'-carbonylbis[1H-imidazole] and 22.3 parts of tetrahydrofuran was stirred for 1½ hour at reflux temperature and overnight at room temperature. The reaction mixture was evaporated and the residue was dissolved in ethyl acetate. This solution was washed successively with water (2×), diluted acetic acid, water (2×) and NaCl (sat.) and was then dried, filtered and evaporated. The residue was purified by flash column chromatography (silica gel; hexane/$CH_3COOC_2H_5$ 3:1). The eluent of the desired fraction was evaporated and the residue was crystallized from acetonitrile. The product was filtered off and dried, yielding 0.36 parts (47.1%) of 9-chloro-4,5,6,7-tetrahydro-7-methyl-6-(3-methyl-2-butenyl)imidazo[4,5,1-jk][1,4]benzodiazepin-2(1H)-one; mp. 138.7° C. (comp. 82).

EXAMPLE 25

A mixture of 19.8 parts of intermediate 23 and 7.2 parts of urea was heated at 210°–220° C. until foaming and $NH_3$ evolution ceased (about 10 min). After cooling to 100° C., there were added 120 parts of HCl (1N). The solution was decanted from the oily residue, boiled with activated charcoal and filtered. After cooling, the filtrate was basified with ammonium hydroxide and extracted with trichloromethane (75 and 150 parts). The combined extracts were dried, filtered and evaporated. The residue was triturated in 2-propanol and was then crystallized from ethanol and from 4-methyl-2-pentanone. The product was filtered off and dried, yielding 2.5 parts (11.5%) of 4,5,6,7-tetrahydro-5-methyl-6-(phenylmethyl)-imidazo[4,5,1-jk][1,4]-benzodiazepin-2(1H)-one; mp. 205° C. (comp. 3).

EXAMPLE 26

To a cooled (0° C.) mixture of 0.93 parts of intermediate 14; 0.86 parts of 4-methylmorpholine and 40 parts of dichloromethane there was added dropwise a solution of 0.43 parts of trichloromethyl chloroformate in 20 parts of dichloromethane under argon. After stirring for ½ hour at 0° C., the product was extracted with a sodium hydrogen carbonate solution. The extract was dried, filtered and evaporated. The residue was purified by flash column chromatography (silica gel; $CH_2Cl_2/CH_3OH$ 15:1). The eluent of the desired fraction was evaporated and the residue was triturated with acetonitrile, yielding 0.32 parts (61.5%) of 4,5,6,7-tetrahydro-7-methyl-6-propylimidazo[4,5,1-jk][1,4]benzodiazepin-2(1H)-one (comp. 40); mp. 124.0° C.

EXAMPLE 27

A mixture of 43.0 parts of intermediate 79; 3152 parts of dichloromethane and 30.1 parts of N,N-diethylethanamine was stirred at 0°–5° C. under a nitrogen atmosphere and screened from light. There was added dropwise a solution of 16.3 parts of thiophosgene in 299 parts of dichloromethane at 0°–5° C. The whole was stirred for 1 hour at 0°–5° C. and was then concentrated to about 1000 ml. The residue was washed with water (2×), dried, filtered and evaporated. The residue was purified by column chromatography (silica gel; $C_6H_5CH_3/CH_3COOC_2H_5$ 88:12). The eluent of the desired fraction was evaporated, yielding 19.5 parts (51.2%) of (+)-(S)-9-chloro-4,5,6,7-tetrahydro-5-methyl-6-(3-methyl-2-butenyl)imidazo[4,5,1-jk][1,4]benzodiazepine-2(1H)-thione; mp. 186.3° C.; $[\alpha]_D^{20} = +11.8°$ (conc.=1% in $CH_3OH$) (comp. 38).

EXAMPLE 28

To a suspension of 1.14 parts of lithium aluminium hydride in 21.8 parts of 1,2-dimethoxyethane there was added a solution of 1.28 parts of intermediate 67 in 21.8 parts of 1,2-dimethoxyethane under argon. After refluxing for 14 hours and subsequent cooling, there were added successively 1.1 parts of water, 3.4 ml of NaOH (3N) and 1.1 parts of water. The whole was stirred for 15 min and was then filtered. The precipitate was washed with dichloromethane and the combined filtrates were dried, filtered and evaporated. The residue was dissolved in 17.8 parts of tetrahydrofuran. There were added 0.9 parts of 1,1'-thiocarbonylbis[1H-imidazole] and the whole was refluxed for 3 hours. The product was extracted with ethyl acetate (9.0 parts) and the extract was washed with water (3×25 parts), dried, filtered and evaporated. The residue was purified by flash column chromatography (silica gel; $CH_2Cl_2/C_2H_5OH$ 99:1). The eluent of the desired fraction was evaporated and the residue was crystallized from acetonitrile. The product was filtered off and dried, yielding 0.20 parts (12.9%) of (+)-(S)-9-chloro-4,5,6,7-tetrahydro-4-methyl-6(2-methyl-2-propenyl)imidazo[4,5,1-jk][1,4]benzodiazepine-2(1H)-thione; mp. 171.4° C.; $[\alpha]_D^{25} = +20.5°$ (conc.=0.77% in $CH_3OH$) (comp. 79).

EXAMPLE 29

To a mixture of 6.84 parts of lithium aluminum hydride and 90 parts of tetrahydrofuran there was added a solution of 9 parts of intermediate 2 in 90 parts of tetrahydrofuran. After stirring for 2½ hour, there were added successively water and NaOH 15% while cooling on ice. The whole was filtered and the filtrate was evaporated. The residue was taken up in methylbenzene and this solution was dried, filtered and evaporated. The residue was heated at 200° C. for 10 min with 2 parts of urea. At 100° C., the whole was diluted with 25 parts of boiling water. The aqueous layer was decanted and the residue was treated with activated charcoal in a mixture of 35 parts of HCl (1N) and 35 parts of water. After filtration, the mixture was basified with $NH_4OH$ and the product was extracted with methylbenzene (80 parts and 40 parts). The combined extracts were dried, filtered and evaporated. The residue was crystallized from 4-methyl-2-pentanone and then converted into the monohydrochloride salt in methanol by addition of 2-propanol saturated with HCl. The salt was filtered off, recrystallized from water and dried, yielding 3.2 parts of 6-(phenylmethyl)-4,5,6,7-tetrahydroimidazo[4,5,1-jk][1,4]benzodiazepin-2(1H)-one monohydrochloride; mp. 258.5°-262° C. (comp. 1).

EXAMPLE 30

A mixture of 0.6 parts of compound 45 and 16.5 parts of phosphoryl chloride was refluxed for 45 min under argon. Gaseous HCl was bubbled through the refluxing mixture for 2 hours. The solvent was evaporated and the residue was diluted with 10 parts of water. After neutralizing with NaHCO$_3$ (sat.), the product was extracted with dichloromethane. The extract was dried, filtered and evaporated and the residue was dissolved in 7.9 parts of ethanol. There was added 1.0 part of thiourea and the whole was refluxed for 3 hours and then evaporated. The residue was partitioned between dichloromethane and water. The organic layer was separated, dried, filtered and evaporated. The residue was purified by flash column chromatography (silica gel; CH$_2$Cl$_2$/C$_2$H$_5$OH 95:5). The eluent of the desired fraction was evaporated and the residue was dried in vacuo at 78° C. overnight, yielding 0.20 parts (31.8%) of (+)-(S)-6-(cyclopropylmethyl)-4,5,6,7-tetrahydro-5-methylimidazo[4,5,1-jk][1,4]benzodiazepine-2(1H)-thione; mp. 197.4° C.; $[\alpha]_D^{25} = +21.4°$ (conc.=0.83% in CHCl$_3$) (comp. 48).

EXAMPLE 31

To a mixture of 0.562 parts of compound 63 and 0.262 parts of sodium carbonate there were added 9.245 parts of phosphoryl chloride under an argon atmosphere. After stirring for 23 hours at 95° C., the reaction mixture was evaporated. The residue was partitioned between dichloromethane and NaHCO$_3$ (sat.). The organic layer was separated, washed with NaHCO$_3$ (sat.) and NaCl (sat.), dried, filtered and evaporated. The residue was mixed with 0.517 parts of thiourea and 7.9 parts of ethanol under argon. After stirring for 22 hours at 95° C., the whole was evaporated and the residue was partitioned again between dichloromethane and NaHCO$_3$ (sat.). The organic layer was washed with NaHCO$_3$ (sat.) and NaCl (sat.), filtered over diatomaceous earth and evaporated. The residue was purified by flash column chromatography (silica gel; CH$_3$COOC$_2$H$_5$/hexane 10:90→40:60). The eluent of the desired fraction was evaporated and the residue was crystallized from ethyl acetate. The product was filtered off and dried in vacuo at 82° C. for 6 hours, yielding 0.21 parts (35.7%) of (S)-9,10-dichloro-4,5,6,7-tetrahydro-5-methyl-6-(3-methyl-2-butenyl)imidazo[4,5,1-jk][1,4]benzodiazepine-2(1H)-thione; mp. 172.8° C. (comp. 64).

EXAMPLE 32

To a cooled (−78° C.) solution of 1.18 parts of compound 99 in 100 parts of dichloromethane under argon, there were added successively and with 15 minutes-intervals 1.26 parts of trifluoroacetic anhydride, 0.61 parts of 2,6-dimethylpyridine and 21.1 ml of 1,1'-oxybisethane, saturated with HCl. The whole was stirred for ½ hour and was then neutralized with NaHCO$_3$ (sat.). The product was extracted with dichloromethane (2×66.5 parts) and the extract was dried, filtered and evaporated. The residue was purified by flash column chromatography (silica gel; CH$_2$Cl$_2$/CH$_3$OH/NH$_4$OH 98:2:01). The eluent of the desired fraction was evaporated and the residue was dissolved in 7.9 parts of ethanol. There were added 2.0 parts of thiourea and the whole was refluxed for 6 hours and then evaporated. The residue was partitioned between water and dichloromethane. The organic layer was separated, washed with NaHCO$_3$ (sat.) and NaCl (sat.), dried, filtered and evaporated. The residue was purified by flash column chromatography (silica gel; hexane/CH$_3$COOC$_2$H$_5$ 75:25). The eluent of the desired fraction was evaporated and the residue was crystallized from acetonitrile. The product was filtered off and dried in vacuo at 60° C., yielding 0.284 parts (20.2%) of (+)-(S)-8-bromo-4,5,6,7-tetrahydro-5-methyl-6-(3-methyl-2-butenyl)imidazo[4,5,1-jk][1,4]benzodiazepine-2(1H)-thione; mp. 161.1° C.; $[\alpha]_D^{25} = +4.6°$ (conc.=1% in CH$_3$OH) (comp. 100).

EXAMPLE 33

To a stirred solution of 1.0 part of intermediate 80 in 39.5 parts of ethanol there were added 0.5 parts of thiourea. Stirring was continued for 20 hours at room temperature under a nitrogen atmosphere and for 3 hours at reflux temperature. The reaction mixture was evaporated and the residue was partitioned between water and dichloromethane. The organic layer was dried, filtered and evaporated, yielding an oily residue. The aqueous layer was basified with NaHCO$_3$ (aq.) and extracted with dichloromethane (3×). The combined extracts were washed with NaCl (sat.), dried, filtered and evaporated, yielding a similar oily residue. The combined oils were purified by flash column chromatography (silica gel; CH$_3$COOC$_2$H$_5$/hexane 25:75). The eluent of the desired fraction was evaporated and the residue was dried in an Abderhalen (i.C$_3$H$_7$OH reflux for 3 hours and at room temperature overnight), yielding 0.41 parts (40.7%) of (±)-4,5,6,7-tetrahydro-5-methyl-6-(3-methyl-2-butenyl)imidazo[4,5,1-jk][1,4]-benzodiazepin-2(1H)-thione; mp. 128.0° C. (comp. 31).

EXAMPLE 34

To a mixture of 1.00 part of intermediate 96; 0.782 parts of sodium carbonate, 0.816 parts of potassium iodide and 94 parts of N,N-dimethylformamide there were added 1.18 parts of 2,3-dibromopropene under an argon atmosphere. The whole was heated at 65°-70° C. for 5 hours under argon and was then evaporated. The residue was partitioned between dichloromethane and water. The organic layer was separated and washed with water. The combined aqueous layers were re-extracted with dichloromethane. The combined organic layers were washed with NaCl (sat.), dried, filtered and evaporated. The residue was dissolved in refluxing acetonitrile and recrystallized upon cooling (2×). The product was filtered off, washed with cold acetonitrile and dried in vacuo at 82° C., yielding 0.762 parts (48.1%) of 6-(2-bromo-2-propenyl)-4,5,6,7-tetrahydro-5-methylimidazo[4,5,1-jk][1,4]benzodiazepin-2(1H)-one; mp. 150.0° C. (comp. 20).

EXAMPLE 35

To a cooled (0° C.) amount of 2.96 parts of trifluoroacetic acid there were added 2.0 parts of intermediate 32 under argon. After stirring for 2 hours at 0° C., the mixture was evaporated. To the residue there were added successively 18.8 parts of N,N-dimethylformamide, 0.86 parts of 1-bromo-3-methyl-2-butene, 3.0 parts of sodium carbonate and 0.96 parts of potassium iodide. The whole was stirred overnight at room temperature and was then evaporated. The residue was partitioned between water and ethyl acetate. The organic layer was separated, washed with NaHCO$_3$ (sat.) and NaCl (sat.), dried, filtered and evaporated. The residue was crystallized from acetonitrile. The product was filtered off and dried in vacuo at 60° C. overnight, yielding 1.5 parts (81.7%) of (+)-(S)-8-bromo-4,5,6,7-tetrahydro-5-methyl-6-(3-methyl-2-butenyl)imidazo[4,5,1-jk][1,4]-benzodiazepin-2-(1H)-one; mp. 125.2° C.; $[\alpha]_D^{25}$ = +12.6° (conc. = 1% in CH$_3$OH) (comp. 99).

EXAMPLE 36

To a stirred mixture of 0.59 parts of intermediate 47; 0.39 parts of sodium carbonate and 4.7 parts of N,N-dimethylformamide were added 0.28 parts of 3-chloro-2-methyl-1-propene under an argon atmosphere. After stirring for 4 days at room temperature, the solvent was evaporated and the residue was taken up in NaCl (sat.). The product was extracted with dichloromethane (3×) and the combined extracts were washed with NaCl (sat.), dried, filtered and evaporated. The residue was purified by column chromatography (silica gel; CH$_2$Cl$_2$/CH$_3$OH 10:1). The eluent of the desired fraction was evaporated and the residue was triturated with acetonitrile, yielding 0.18 parts (24.7%) of 9-chloro-4,5,6,7-tetrahydro-5-methyl-6-(2-methyl-2-propenyl-)imidazo[4,5,1-jk][1,4]benzodiazepin-2(1H)-one; mp. 174.9° C. (comp. 35).

EXAMPLE 37

A mixture of 6.1 parts of intermediate 96; 6.7 parts of 2-bromoethylbenzene, 3.6 parts of N,N-diethylethanamine, a few crystals of potassium iodide and 80 parts of 1-butanol was stirred for 24 hours at reflux temperature. The reaction mixture was evaporated and the residue was diluted with 100 parts of water. The product was extracted with trichloromethane (2×75 parts) and the combined extracts were dried, filtered and evaporated. The residue was successively crystallized from 4-methyl-2-pentanone (2×) and from methanol. The product was filtered off and dried, yielding 3.4 parts of 4,5,6,7-tetrahydro-5-methyl-6-phenylethylimidazo[4,5,1-jk][1,4]benzodiazepin-2(1H)-one; mp. 150° C. (comp. 4).

EXAMPLE 38

To a stirred and cooled (−60° to −50° C.) amount of 45.3 parts of concentrated nitric acid there were added portionwise 2.75 parts of compound 45 under an argon atmosphere. When a clear solution was obtained, stirring and cooling was continued for ½ hour. The reaction mixture was slowly poured into 400 parts of ice-water and the whole was basified to pH 8 with Na$_2$CO$_3$. The precipitated product was filtered off and dried in vacuo at 50° C. for 16 hours, yielding 0.5 parts (15.6%) of a mixture of (S)-6-(cyclopropylmethyl)-4,5,6,7-tetrahydro-5-methyl-9-nitroimidazo[4,5,1-jk][1,4]benzodiazepin-2(1H)-one and the 8-nitro-isomer thereof (75:25) (comp. 67).

EXAMPLE 39

To a refluxing mixture of 1.03 parts of hydrazine monohydrate, 23.7 parts of methanol and 0.15 parts of Raney nickel there were added portionwise 0.5 parts of compound 67. After refluxing for 20 min and subsequent cooling, the reaction mixture was filtered over diatomaceous earth and the filtrate was evaporated. The residue was purified by preparative thin layer chromatography (eluens: CH$_2$Cl$_2$/CH$_3$OH 90:10). The eluent of the pure fractions was evaporated and the residue was dried in vacuo at 50° C. for 16 hours, yielding 0.17 parts (39.0%) of (+)-(S)-9-amino-6-(cyclopropylmethyl)-4,5,6,7-tetrahydro-5-methylimidazo[4,5,1-jk][1,4]benzodiazepin-2(1H)-one; mp. 188.7° C.; $[\alpha]_D^{25}$ = +13.4° (conc. = 0.50% in trichloromethane) (comp. 68).

EXAMPLE 40

To a stirred solution of 0.32 parts of compound 68 in 26.7 parts of tetrahydrofuran there were added 0.093 parts of acetyl chloride. Stirring was continued for 16 hours at room temperature. The reaction mixture was evaporated and the residue was basified with Na$_2$CO$_3$ (sat.). The product was extracted with trichloromethane and the extract was dried, filtered and evaporated. The residue was purified by flash column chromatography (silica gel; CH$_2$Cl$_2$/CH$_3$OH 100:0→97:3). The eluent of the desired fraction was evaporated and the residue was dried in vacuo at 50° C. for 16 hours, yielding 0.18 parts (47.7%) of (+)-(S)-N-[6-(cyclopropylmethyl)-1,2,4,5,6,7-hexahydro-5-methyl-2-oxoimidazo[4,5,1-jk][1,4]benzodiazepin-9-yl]acetamide; mp. 243.9° C.; $[\alpha]_D^{25}$ = +15.1° (conc. = 0.43% in methanol) (comp. 81).

All the other compounds listed in Table 3 were obtained by analogous methods of preparation as described in Ex. 21–40, the actual method of preparation being indicated in column 2 (Ex. No.).

TABLE 3

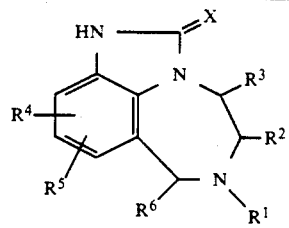

| Co. No. | Ex. No. | X | R$^1$ | R$^2$ | R$^3$ | R$^4$ | R$^5$ | R$^6$ | physical data |
|---|---|---|---|---|---|---|---|---|---|
| 1 | 29 | O | C$_6$H$_5$—CH$_2$— | H | H | H | H | H | 258.5–262° C. HCl |
| 2 | 37 | O | C$_6$H$_5$—(CH$_2$)$_2$— | H | H | H | H | H | 165.5° C. |
| 3 | 25 | O | C$_6$H$_5$—CH$_2$— | CH$_3$ | H | H | H | H | 205° C. |
| 4 | 37 | O | C$_6$H$_5$—(CH$_2$)$_2$— | CH$_3$ | H | H | H | H | 150° C. |
| 5 | 37 | O | CH$_2$=CH—CH$_2$— | CH$_3$ | H | H | H | H | 138° C. |
| 6 | 34 | O | CH$_2$—C(CH$_3$)—CH$_2$— | CH$_3$ | H | H | H | H | 150.1° C. |
| 7 | 34 | O | CH≡C—CH$_2$— | CH$_3$ | H | H | H | H | 146.0° C. |
| 8 | 34 | O | CH$_2$=CH—CH$_2$— | CH$_3$ | H | H | H | H | 113.8° C. |

TABLE 3-continued

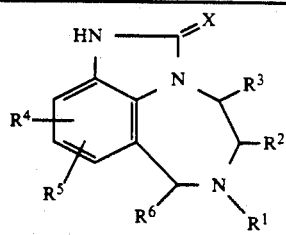

| Co. No. | Ex. No. | X | $R^1$ | $R^2$ | $R^3$ | $R^4$ | $R^5$ | $R^6$ | physical data |
|---|---|---|---|---|---|---|---|---|---|
| 9 | 34 | O | $CH_2$=CH—$(CH_2)_2$— | $CH_3$ | H | H | H | H | (+)-(S) 107.2° C. |
| 10 | 34 | O | $C_3H_7$— | $CH_3$ | H | H | H | H | 149.7° C. |
| 11 | 36 | O | $C_2H_5$— | $CH_3$ | H | H | H | H | 143.2° C./(+) |
| 12 | 34 | O | $CH_2$=C($CH_3$)—$CH_2$— | $CH_3$ | H | H | H | H | 152.4° C. |
| 13 | 34 | O | c.$C_3H_5$—$CH_2$— | $CH_3$ | H | H | H | H | (+)-(S) 97.6° C./$H_2O$ |
| 14 | 34 | O | $CH_2$=C($CH_3$)—$CH_2$— | H | $CH_3$ | H | H | H | 142.1° C. |
| 15 | 34 | O | $CH_3$—CH=CH—$CH_2$— | $CH_3$ | H | H | H | H | 127.6° C./(E) |
| 16 | 34 | O | $CH_3$—CH=CH—$CH_2$— | $CH_3$ | H | H | H | H | 106.0° C./(Z) |
| 17 | 34 | O | $(CH_3)_2$CH—$CH_2$— | $CH_3$ | H | H | H | H | 119.7° C. ½$H_2O$ |
| 18 | 34 | O | $C_4H_9$— | $CH_3$ | H | H | H | H | 138.0° C. |
| 19 | 34 | O | $(CH_3)_2$C=CH—$CH_2$— | $CH_3$ | H | H | H | H | 158.0° C./(±) |
| 20 | 34 | O | $CH_2$=C(Br)—$CH_2$— | $CH_3$ | H | H | H | H | 150.0° C. |
| 21 | 34 | O | $CH_3CH$=C($CH_3$)—$CH_2$— | $CH_3$ | H | H | H | H | 151.6° C. (±)-(E) |
| 22 | 21 | S | $CH_3$—$(CH_2)_2$— | $CH_3$ | H | H | H | H | 149-151° C. |
| 23 | 34 | O | $CH_2$=C($CH_3$)—$CH_2$— | $CH_3$ | H | 9-$CH_3$ | H | H | 154.2° C. |
| 24 | 34 | O | $C_3H_7$— | H | $(CH_3)_2$CH— | H | H | H | 138.6° C. |
| 25 | 34 | O | $CH_2$=C($CH_3$)—$CH_2$— | H | $(CH_3)_2$CH— | H | H | H | 142.6° C. |
| 26 | 34 | O | $(CH_3)_2$C=CH—CH— | $CH_3$ | H | H | H | H | 125.1° C. |
| 27 | 34 | O | $(CH_3)_2$C=CH—CH— | $CH_3$ | H | H | H | H | (−)-(R) 136.4° C. |
| 28 | 34 | O | $C_3H_7$— | H | $C_3H_7$— | H | H | H | (+)-(S) 119.0° C. |
| 29 | 34 | O | $CH_2$=C($CH_3$)—$CH_2$— | H | $C_3H_7$— | H | H | H | 132.2° C. |
| 30 | 34 | O | $CH_2$=C($CH_3$)—$CH_2$— | $CH_3$ | H | 8-$CH_3$ | H | H | 170.6° C. |
| 31 | 33 | S | $(CH_3)_2$C=CH—CH— | $CH_3$ | H | H | H | H | 128.0° C./(±) |
| 32 | 34 | O | $(CH_3)_2$C=C($CH_3$)—$CH_2$— | $CH_3$ | H | H | H | H | 180.6° C. |
| 33 | 34 | O | $CH_2$=C($C_2H_5$)—$CH_2$— | $CH_3$ | H | H | H | H | 109.1° C. |
| 34 | 34 | O | $(CH_3)_2CHC$(=$CH_2$)$CH_2$— | $CH_3$ | H | H | H | H | 142.2° C. |
| 35 | 36 | O | $CH_2$=C($CH_3$)—$CH_2$— | $CH_3$ | H | 9-Cl | H | H | 174.9° C. |
| 36 | 33 | S | $(CH_3)_2$C=CH—CH— | $CH_3$ | H | H | H | H | 174.5° C./(+)-(S) $[α]_D^{20}$ 1% EtOH = +15.9° |
| 37 | 34 | O | $(CH_3)_2$C=CH—$CH_2$— | $CH_3$ | H | 9-Cl | H | H | 135.6° C./(+)-(S) $[α]_D^{20}$ 0.96 MeOH = +7.7° |
| 38 | 27 | S | $(CH_3)_2$C=CH—$CH_2$— | $CH_3$ | H | 9-Cl | H | H | 186.3° C./(+)-(S) $[α]_D^{20}$ 1% MeOH = +11.8° |
| 39 | 33 | S | $(CH_3)_2$C=CH—$CH_2$— | $CH_3$ | H | H | H | H | 178.5° C. (−)-(R) $[α]_{0.1\% EtOH}^{25}$ = −16.4° |
| 40 | 26 | O | $C_3H_7$— | H | H | H | H | $CH_3$ | 124.0° C. |
| 41 | 21 | S | $C_3H_7$— | H | H | H | H | $CH_3$ | 179.1° C. |
| 42 | 34 | O | $(CH_3)_2$C=CH—$CH_2$— | $CH_3$ | H | 9-Cl | H | H | 134.4° C. (−)-(R) $[α]_D^{20}$ 0.87% MeOH = −8.85° |
| 43 | 21 | S | $(CH_3)_2$C=CH—$CH_2$— | H | H | H | H | $CH_3$ | 192.4° C. |
| 44 | 26 | O | $(CH_3)_2$C=CH—$CH_2$— | H | H | H | H | $CH_3$ | 108.8° C. |
| 45 | 34 | O | c.$C_3H_5$—$CH_2$— | $CH_3$ | H | H | H | H | 115.9° C. (+)-(S) |
| 46 | 33 | S | $(CH_3)_2$C=CH—$CH_2$— | $CH_3$ | H | 9-Cl | H | H | >270° C. (+)-(S)/HCl |
| 47 | 30 | S | $CH_2$=C($CH_3$)—$CH_2$— | $CH_3$ | H | H | H | H | 137.6° C. (+)-(S) |
| 48 | 30 | S | c.$C_3H_5$—$CH_2$— | $CH_3$ | H | H | H | H | 197.4° C. $[α]_D^{25}$ 1.09% MeOH = +26.2° (+)-(S) |
| 49 | 34 | O | $(CH_3)_2$C=CH—$CH_2$— | $CH_3$ | H | 8-$CH_3$ | H | H | 189.7° C. $[α]_D^{25}$ 0.83% CHCl3 = +21.4° (+)-(S) |
| 50 | 33 | S | $(CH_3)_2$C=CH—$CH_2$— | $CH_3$ | H | 8-$CH_3$ | H | H | 147.6° C. $[α]_D^{25}$ 0.88% MeOH = +8.8° (+)-(S) |
| 51 | 22 | S | $(CH_3)_2$C=CH—$CH_2$— | $CH_3$ | $CH_3$ | H | H | H | 156.0° C./trans $[α]_D^{25}$ 0.33% MeOH = +7.4° |
| 52 | 22 | S | $(CH_3)_2$C=CH—$CH_2$— | $CH_3$ | H | H | H | $CH_3$ | 138.3° C./cis |
| 53 | 22 | S | $(CH_3)_2$C=CH—$CH_2$— | $CH_3$ | H | H | H | $CH_3$ | 138.8° C./trans |

TABLE 3-continued

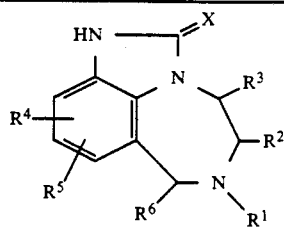

| Co. No. | Ex. No. | X | R¹ | R² | R³ | R⁴ | R⁵ | R⁶ | physical data |
|---|---|---|---|---|---|---|---|---|---|
| 54 | 33 | S | (CH₃)₂C=CH—CH₂— | CH₃ | H | 9-Cl | H | H | 183.2° C. (−)-(R) $[\alpha]_D^{25}$ 0.86% MeOH = −9.2° |
| 55 | 22 | S | (CH₃)₂C=CH—CH₂— | H | CH₃ | H | H | CH₃ | 191.4° C. (4,7-trans) |
| 56 | 22 | S | (CH₃)₂C=CH—CH₂— | H | CH₃ | H | H | CH₃ | 185.2° C. (4,7-cis) |
| 57 | 23 | S | c.C₃H₅—CH₂— | CH₃ | CH₃ | H | H | H | 135.2° C. (4,5-trans) |
| 58 | 34 | O | (CH₃)₂C=CH—CH₂— | H | H | 9-Cl | H | H | 128-131° C. |
| 59 | 33 | S | (CH₃)₂C=CH—CH₂— | H | H | 9-Cl | H | H | 226.2° C. |
| 60 | 21 | S | c.C₃H₅—CH₂— | CH₃ | H | 9-Cl | H | H | 173.5° C. (+)-(S) $[\alpha]_D^{25}$ % MeOH = +12.9° |
| 61 | 34 | O | (CH₃)₂C=CH—CH₂— | CH₃ | H | 9-F | H | H | 142-148° C. (+)-(S) $[\alpha]_D^{25}$ 1% CHCl₃ = +6.6° |
| 62 | 33 | S | (CH₃)₂C=CH—CH₂— | CH₃ | H | 9-F | H | H | 174.5° C. (+)-(S) $[\alpha]_D^{25}$ 1% CHCl₃ = +7.3 |
| 63 | 36 | O | (CH₃)₂C=CH—CH₂— | CH₃ | H | 9-Cl | 10-Cl | H | (S)/(Z)** |
| 64 | 31 | S | (CH₃)₂C=CH—CH₂— | CH₃ | H | 9-Cl | 10-Cl | H | 172.8° C./(S) |
| 65 | 36 | O | (C₂H₅)₂C=CH—CH₂— | CH₃ | H | 9-Cl | H | H | 239.4° C. (−)-(S)/HCl $[\alpha]_D^{25}$ 1% MeOH = −7.9° |
| 66 | 34 | O | c.C₄H₇—CH₂— | CH₃ | H | 9-Cl | H | H | 139.3° C. (−)-(S) $[\alpha]_D^{25}$ 0.46% MeOH = −3.05° |
| 67 | 38 | O | c.C₃H₅—CH₂— | CH₃ | H | 9-NO₂ | H | H | (S) |
| 68 | 39 | O | c.C₃H₅—CH₂— | CH₃ | H | 9-NH₂ | H | H | 188.7° C. (+)-(S) $[\alpha]_D^{25}$ 0.5% CHCl₃ = +13.4° |
| 69 | 33 | S | c.C₄H₇—CH₂— | CH₃ | H | 9-Cl | H | H | 206.8° C. (−)-(S) $[\alpha]_D^{25}$ 0.47% MeOH = −0.6° |
| 70 | 36 | O | Cl—CH=CH—CH₂— | CH₃ | H | 9-Cl | H | H | 145.7° C. (−)-[S(E)] $[\alpha]_D^{25}$ 0.5% CHCl₃ = −17.0° |
| 71 | 36 | O | Cl—CH=CH—CH₂— | CH₃ | H | 9-Cl | H | H | 141.2° C. (+)-[S(Z)] $[\alpha]_D^{25}$ 0.5% CHCl₃ = +35.6° |
| 72 | 36 | O | (C₂H₅)₂C=CH—CH₂— | CH₃ | H | 8-CH₃ | H | H | 117.3° C. (+)-(S) $[\alpha]_D^{25}$ 1% MeOH = +4.9° |
| 73 | 34 | O | c.C₃H₅—(CH₂)₂— | CH₃ | H | 9-Cl | H | H | 127.7° C. (−)-(S) $[\alpha]_D^{25}$ 1% MeOH = −8.0° |
| 74 | 34 | O | (C₂H₅)₂C=CH—CH₂— | CH₃ | H | 9-CH₃ | H | H | 103.0° C./(±) |
| 75 | 34 | O | CH₂=CH—(CH₂)₄— | CH₃ | H | 9-Cl | H | H | 127.9° C./(−)-(s) $[\alpha]_D^{25}$ 1% MeOH = −11.0° |
| 76 | 34 | O | CH₂=CH—(CH₂)₃— | CH₃ | H | 9-Cl | H | H | 107.5° C./(−)-(S) $[\alpha]_D^{25}$ 1% MeOH = −7.4° |
| 77 | 33 | S | c.C₃H₅—(CH₂)₂— | CH₃ | H | 9-Cl | H | H | 174.8° C./(−)-(S) $[\alpha]_D^{25}$ 1% MeOH = −4.7° |
| 78 | 28 | S | c.C₃H₅—CH₂— | H | CH₃ | 9-Cl | H | H | 210.9° C./(−)-(R) $[\alpha]_D^{25}$ = −7.9° c = 0.23% MeOH—CHCl₃ (3.6:1) |
| 79 | 28 | S | CH₂=C(CH₃)—CH₂— | H | CH₃ | 9-Cl | H | H | 171.4° C./(+)-(S) $[\alpha]_D^{25}$ 0.77% MeOH = +20.5° |
| 80 | 33 | S | (C₂H₅)₂C=CH—CH₂— | CH₃ | H | 9-Cl | H | H | >280° C./(−)-(S) HCl |
| 81 | 40 | O | c.C₃H₅—CH₂— | CH₃ | H | 9-* | H | H | 243.9° C./(+)-(S) $[\alpha]_D^{25}$ 1% MeOH = −32.7° |
| 82 | 24 | O | (CH₃)₂C=CH—CH₂— | H | H | 9-Cl | H | CH₃ | 138.7° C. $[\alpha]_D^{25}$ 0.43% MeOH = +15.1° |
| 83 | 22 | S | (CH₃)₂C=CH—CH₂— | H | H | 9-Cl | H | CH₃ | 197.4° C. |
| 84 | 34 | O | (CH₃)₂C=CH—CH₂— | CH₃ | H | 9-CF₃ | H | H | 125.4° C./(S) |

TABLE 3-continued

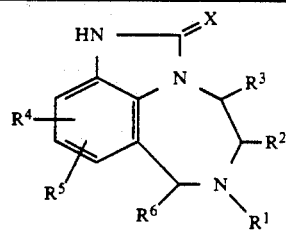

| Co. No. | Ex. No. | X | R¹ | R² | R³ | R⁴ | R⁵ | R⁶ | physical data |
|---|---|---|---|---|---|---|---|---|---|
| 85 | 33 | S | $(CH_3)_2C=CH-CH_2-$ | $CH_3$ | H | 9-$CF_3$ | H | H | 148.3° C./(S) |
| 86 | 22 | S | $(CH_3)_2C=CH-CH_2-$ | $CH_3$ | H | 8-Cl | H | H | 163.3° C./(S) |
| 87 | 23 | O | $(CH_3)_2CH-(CH_2)_2-$ | $CH_3$ | H | 9-Cl | H | H | 257.9° C./(−)-(S)/HCl $[\alpha]_D^{25}$ 0.1% MeOH = −2.95° C. |
| 88 | 31 | S | $c.C_3H_5-CH_2-$ | $CH_3$ | H | 9-$NO_2$ | H | H | 202.8° C./(+)-(S) $[\alpha]_D^{25}$ = +6.5° (c = 0.17% $CHCl_3$—MeOH) (3-1) |
| 89 | 34 | O | $(Cl)_2C=CH-CH_2-$ | $CH_3$ | H | 9-Cl | H | H | 151.7° C./(+)-(S) $[\alpha]_D^{25}$ 1% MeOH = +12.8° |
| 90 | 36 | O | $(C_3H_7)_2C=CH-CH_2-$ | $CH_3$ | H | 9-Cl | H | H | 200.5° C. (−)-(S)/HCl $[\alpha]_D^{25}$ 1% MeOH = −8.2° |
| 91 | 39 | O | $c.C_3H_5-CH_2-$ | $CH_3$ | H | 8-$NH_2$ | H | H | 206.0° C./(+)-(S) $[\alpha]_D^{25}$ 0.44% MeOH = +4.5° |
| 92 | 40 | O | $c.C_3H_5-CH_2-$ | $CH_3$ | H | 8-* | H | H | 227.6° C. (−)-(S) $[\alpha]_D^{25}$ 0.44% MeOH = −1.8° |
| 93 | 36 | O | cyclohexyl=CH—$CH_2$— | $CH_3$ | H | 9-Cl | H | H | 216.6° C. (−)-(S)/HCl $[\alpha]_D^{25}$ 1% MeOH = −7.4° |
| 94 | 34 | O | $(CH_3)_2C=CH-CH_2-$ | $CH_3$ | $CH_3$ | H | H | H | 151.1° C. |
| 95 | 33 | S | $(CH_3)_2C=CH-CH_2-$ | $CH_3$ | $CH_3$ | H | H | H | 162.0° C. (4,5 cis) |
| 96 | 36 | O | $(i.C_3H_7)_2C=CH-CH_2-$ | $CH_3$ | H | 9-Cl | H | H | 205.8° C. (−)-(S)/HCl $[\alpha]_D^{25}$ 1% MeOH = −4.0° |
| 97 | 34 | O | $c.C_5H_9-CH_2-$ | $CH_3$ | H | 9-Cl | H | H | 186.5° C. (−)-(S) $[\alpha]_D^{25}$ 0.78% MeOH = −8.9° |
| 98 | 35 | O | $(CH_3)_2C=CH-CH_2-$ | $CH_3$ | H | 10-Br | H | H | 163.3° C. (−)-(S) $[\alpha]_D^{25}$ 0.95% MeOH = −4.1° |
| 99 | 35 | O | $(CH_3)_2C=CH-CH_2-$ | $CH_3$ | H | 8-Br | H | H | 125.2° C. (+)-(S) $[\alpha]_D^{25}$ 1% MeOH = +12.6° |
| 100 | 32 | S | $(CH_3)_2C=CH-CH_2-$ | $CH_3$ | H | 8-Br | H | H | 161.1° C. (+)-(S) $[\alpha]_D^{25}$ 1% MeOH = +4.6° |
| 101 | 33 | S | $(CH_3)_2CH-CH_2-CH_2-$ | $CH_3$ | H | 9-Cl | H | H | 169.5° C. (−)-(S) $[\alpha]_D^{25}$ 0.1% MeOH = −4.53° |
| 102 | 34 | O | $(CH_3)_2C=CH-(CH_2)_2-$ | $CH_3$ | H | 9-Cl | H | H | 208.8° C./(S)/ HCl $[\alpha]_D^{25}$ 0.1% MeOH = 0 |
| 103 | 22 | S | $(CH_3)_2C=CH-CH_2-$ | $CH_3$ | H | 9-Cl | H | $CH_3$ | 212.1° C. (+)[5S(5α, 7β)] HCl $[\alpha]_D^{25}$ 0.1% MeOH = +57.9° |
| 104 | 26 | O | $(CH_3)_2C=CH-CH_2-$ | $CH_3$ | H | 9-Cl | H | $CH_3$ | 218.8° C. (+)[5S(5α, 7β)] HCl $[\alpha]_D^{25}$ 0.1% MeOH = +44.3° |
| 105 | 33 | S | $c.C_5H_9-CH_2-$ | $CH_3$ | H | 9-Cl | H | H | 204.1° C. (−)-(S) $[\alpha]_D^{25}$ 0.73% MeOH = −5.9° |
| 106 | 26 | O | $(C_2H_5)_2C=CH-CH_2-$ | $CH_3$ | H | 8-Cl | H | H | 156.8° C. (+)-(S) $[\alpha]_D^{25}$ 0.1% MeOH = +7.15° |
| 107 | 33 | S | $(C_2H_5)_2C=CH-CH_2-$ | $CH_3$ | H | 8-Cl | H | H | 113.5° C./(+)-(S) $[\alpha]_D^{25}$ 0.1% MeOH = +0.91° |

TABLE 3-continued

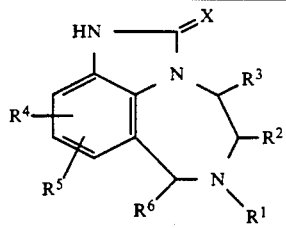

| Co. No. | Ex. No. | X | R¹ | R² | R³ | R⁴ | R⁵ | R⁶ | physical data |
|---|---|---|---|---|---|---|---|---|---|
| 108 | 22 | S | $(CH_3)_2C=CH-CH_2-$ | H | H | 8-Cl | H | H | 215.4° C. |

*$CH_3CONH-$
**2-butenedioate

C. Pharmacological example

EXAMPLE 41

A rapid, sensitive and automated assay procedure [Journal of Virological Methods, 20, 309–321 (1988)] was used for the in-vitro evaluation of anti-HIV agents. An HIV-1 transformed T4-cell line, MT-4, which was previously shown (Koyanagi et al., Int. J. Cancer, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in-situ reduction of 3-(4,5-dimethylthiazol-2-yl)-2,5-diphenyltetrazolium bromide (MTT). The 50% cytotoxic dose ($CD_{50}$ in µg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% effective dose ($ED_{50}$ in µg/ml). The ratio of $CD_{50}$ to $ED_{50}$ was defined as the selectivity index (SI).

TABLE 4

50% cytotoxic ($CD_{50}$), 50% effective dose ($ED_{50}$) and selectivity index (SI).

| Comp. No. | $CD_{50}$ (µg/ml) | $ED_{50}$ (µg/ml) | SI |
|---|---|---|---|
| 31 | 25 | 0.013 | 1923 |
| 36 | 325 | 0.008 | 40625 |
| 38 | 10 | 0.005 | 2000 |
| 39 | ≧250 | 0.045 | ≧5555 |
| 43 | 177 | 0.10 | 1770 |
| 46 | 16 | 0.0066 | 2424 |
| 48 | >250 | 0.0166 | >15029 |
| 50 | 22 | 0.0041 | 5366 |
| 51 | 14.3 | 0.038 | 370 |
| 53 | 23 | 0.0048 | 4838 |
| 54 | 5.5 | 0.094 | 58 |
| 59 | 199 | ≦0.028 | ≧7107 |
| 62 | 24.7 | 0.0076 | 3250 |
| 80 | 5.2 | 0.006 | 850 |
| 83 | 10 | 0.01 | 1000 |
| 86 | 15.7 | 0.001 | 15700 |
| 100 | 25.4 | 0.0011 | 23090 |

D. Composition Examples

EXAMPLE 42

ORAL SOLUTION 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the active ingredient per teaspoonful (5 ml). The resulting solution is filled in suitable containers.

EXAMPLE 43

CAPSULES 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, comprising each 20 mg of the active ingredient.

EXAMPLE 44

FILM-COATED TABLETS

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90 ®) in about 200 ml of water. The wet powder mixture is sieved, dried and sieved again. Then there are added 100 g microcrystalline cellulose (Avicel ®) and 15 g hydrogenated vegetable oil (Sterotex ®). The whole is mixed well and compressed into tablets, giving 10.000 tablets, each containing 10 mg of the active ingredient.

Coating

To a solution of 10 g methyl cellulose (Methocel 60 HG ®) in 75 ml of denatured ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109 ®) and the whole is homogenated. The tablet cores are coated with the thus obtained mixture in a coating apparatus.

EXAMPLE 45

INJECTABLE SOLUTION 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l, giving a solution comprising 4 mg/ml of A.I. The solution is sterilized by filtration (U.S.P. XVII p. 811) and filled in sterile containers.

We claim:

1. A compound having the formula:

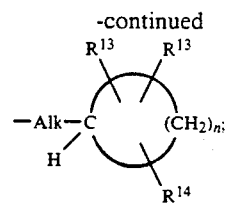
(I)

a pharmaceutically acceptable acid addition salt or a stereochemically isomeric form thereof, wherein:

X is O or S;

$R^1$ is $C_{1-6}$alkyl optionally substituted with aryl; $C_{3-6}$alkynyl; $C_{3-6}$cycloalkyl; or a radical of formula:

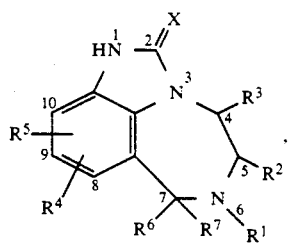
(a-1)

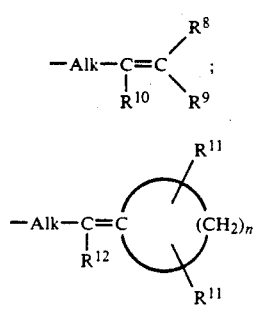
(a-2)

or

-continued (a-3)

Alk is $C_{1-6}$alkanediyl;

$R^8$ and $R^9$ each independently are hydrogen, halo, $C_{3-6}$cycloalkyl, trifluoromethyl, 2,2,2-trifluoroethyl, $C_{1-4}$alkyl optionally substituted with $C_{1-4}$alkyloxy;

$R^{10}$ is hydrogen, halo or $C_{1-4}$alkyl;

each $R^{11}$ independently is hydrogen or $C_{1-4}$alkyl; or both $R^{11}$ taken together may form a $C_{1-6}$alkanediyl radical;

$R^{12}$ is hydrogen, halo or $C_{1-4}$alkyl;

n is 2, 3, 4, 5 or 6;

each $R^{13}$ independently is hydrogen or $C_{1-4}$alkyl; or both $R^{13}$ taken together may form a $C_{1-6}$alkanediyl radical;

$R^{14}$ is hydrogen or $C_{2-6}$alkenyl;

$R^2$ is hydrogen or methyl;

$R^3$ is hydrogen or $C_{1-6}$alkyl;

$R^4$ and $R^5$ each independently are hydrogen, $C_{1-6}$alkyl, halo, cyano, nitro, trifluoromethyl, hydroxy, $C_{1-6}$alkyloxy, amino, mono- or di($C_{1-6}$alkyl)amino or $C_{1-6}$alkylcarbonylamino;

$R^6$ is hydrogen or methyl;

$R^7$ is hydrogen or methyl;

each aryl is phenyl optionally substituted with from 1 to 3 substituents independently selected from $C_{1-6}$alkyl, halo, hydroxy, $C_{1-6}$alkyloxy, amino, nitro and trifluoromethyl, provided that the compounds 6-allyl-4,5,6,7-tetrahydroimidazo[4,5,1-jk][1,4]benzodiazepin-2(1H)-one and (R)-4,5,6,7-tetrahydro-5-methyl-6-(2-propenyl)imidazo[4,5,1-jk][1,4]benzodiazepin-2(1H)-one are excluded.

2. A compound according to claim 1 wherein $R^1$ is $C_{1-6}$alkyl, $C_{3-6}$alkenyl, $C_{3-6}$alkynyl, $C_{3-6}$cycloalkyl or $C_{1-6}$alkyl substituted with $C_{3-6}$cycloalkyl; $R^4$ and $R^5$ each independently are hydrogen, $C_{1-6}$alkyl, halo, cyano, nitro, trifluoromethyl, hydroxy, $C_{1-6}$alkyloxy, amino or mono- or di($C_{1-6}$alkyl)amino; and $R^6$ and $R^7$ are hydrogen.

3. A compound according to claim 1 wherein $R^1$ is $C_{1-6}$alkyl, $C_{3-6}$alkenyl, $C_{3-6}$alkynyl, $C_{3-6}$cycloalkyl or $C_{1-6}$alkyl substituted with $C_{3-6}$cycloalkyl; $R^4$ and $R^5$ each independently are hydrogen, $C_{1-6}$alkyl, halo, cyano, nitro, trifluoromethyl, hydroxy, $C_{1-6}$alkyloxy, amino or mono- or di($C_{1-6}$alkyl)amino; and $R^6$ is methyl, $R^7$ is hydrogen.

4. A compound according to claim 1 wherein $R^1$ is $C_{1-6}$alkyl, $C_{3-6}$alkynyl or a radical of formula (a-1), (a-2) or (a-3); and $R^4$ and $R^5$ each independently are hydrogen, $C_{1-6}$alkyl, halo, cyano, nitro, amino, trifluoromethyl, hydroxy or $C_{1-6}$alkyloxy.

5. A compound according to claim 4 wherein $R^2$ and $R^3$ each independently are hydrogen or methyl; and X is O.

6. A compound according to claim 4 wherein $R^2$ and $R^3$ each independently are hydrogen or methyl; and X is S.

7. A compound according to claim 6 wherein $R^1$ is $C_{3-6}$alkyl or a radical of formula (a-1) wherein $R^8$ and $R^9$ each independently are $C_{3-6}$cycloalkyl, trifluoromethyl or $C_{1-4}$alkyl; or a radical of formula (a-3) wherein n is 2 or 3; and $R^5$ and $R^7$ are hydrogen.

8. A compound according to claim 7 wherein $R^8$ and $R^9$ each independently are $C_{1-3}$alkyl; each $R^{13}$ and $R^{14}$ are hydrogen; and $R^6$ is hydrogen.

9. A compound according to claim 8 wherein $R^1$ is propyl; 3,3-dimethylbutyl; methylcyclopropyl optionally substituted with one or two methyl groups or one 2-methylpropenyl group; methylcyclobutyl; 2-propenyl; 2-butenyl; 2-methyl-2-butenyl; 3-methyl-2-butenyl, 2,3-dimethyl-2-butenyl or 3-ethyl-2-pentenyl; and $R^4$ is hydrogen, methyl, chloro or bromo.

10. A compound according to claim 1 wherein the compound is
(+)-(S)-9-chloro-4,5,6,7-tetrahydro-5-methyl-6-(3-methyl-2-butenyl)imidazo[4,5,1-jk][1,4]benzodiazepine-2(1H)-thione;
(+)-(S)-4,5,6,7-tetrahydro-5,8-dimethyl-6-(3-methyl-2-butenyl)imidazo[4,5,1-jk][1,4]benzodiazepine-2(1H)-thione;
(+)-(S)-8-bromo-4,5,6,7-tetrahydro-5-methyl-6-(3-methyl-2-butenyl)imidazo[4,5,1-jk][1,4]benzodiazepine-2(1H)-thione;
(+)-(S)-8-chloro-6-(3-ethyl-2-pentenyl)-4,5,6,7-tetrahydro-5-methylimidazo[4,5,1-jk][1,4]benzodiazepine-2(1H)-thione and
(+)-(S)-8-chloro-4,5,6,7-tetrahydro-5-methyl-6-(3-methyl-2-butenyl)imidazo[4,5,1-jk][1,4]benzodiazepine-2(1H)-thione.

11. A compound having the formula:

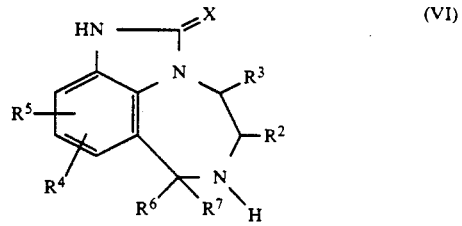

a pharmaceutically acceptable acid addition salt or a stereochemically isomeric form thereof, wherein
X is O or S;
$R^2$ is hydrogen or methyl;
$R^3$ is hydrogen or $C_{1-6}$alkyl;
$R^4$ and $R^5$ each independently are hydrogen, $C_{1-6}$alkyl, halo, cyano, nitro, trifluoromethyl, hydroxy, $C_{1-6}$alkyloxy, amino, mono- or di($C_{1-6}$alkyl)amino or $C_{1-6}$alkylcarbonylamino;
$R^6$ is hydrogen or methyl;
$R^7$ is hydrogen or methyl; and
each aryl is phenyl optionally substituted with from 1 to 3 substituents independently selected from $C_{1-6}$alkyl, halo, hydroxy, $C_{1-6}$alkyloxy, amino, nitro and trifluoromethyl.

* * * * *

UNITED STATES PATENT AND TRADEMARK OFFICE
CERTIFICATE OF CORRECTION

PATENT NO. : 5,270,464
DATED : December 14, 1993
INVENTOR(S) : Michael J. Kukla, et al.

It is certified that error appears in the above-indentified patent and that said Letters Patent is hereby corrected as shown below:

Claim 10, line 17, after "is" insert
--selected from the group consisting of:--.

Signed and Sealed this

Third Day of August, 1999

Attest:

Attesting Officer

Q. TODD DICKINSON

Acting Commissioner of Patents and Trademarks